(12) United States Patent
Zucherman et al.

(10) Patent No.: US 7,862,569 B2
(45) Date of Patent: *Jan. 4, 2011

(54) SYSTEM AND METHOD FOR STRENGTHENING A SPINOUS PROCESS

(75) Inventors: James F. Zucherman, San Francisco, CA (US); Ken Y. Hsu, San Francisco, CA (US); Steven T. Mitchell, Pleasant Hill, CA (US); Scott A. Yerby, Montara, CA (US)

(73) Assignee: Kyphon SARL, Neuchâtel (CH)

( * ) Notice: Subject to any disclaimer, the term of this patent is extended or adjusted under 35 U.S.C. 154(b) by 899 days.

This patent is subject to a terminal disclaimer.

(21) Appl. No.: 11/737,685

(22) Filed: Apr. 19, 2007

(65) Prior Publication Data
US 2008/0027435 A1  Jan. 31, 2008

Related U.S. Application Data

(60) Provisional application No. 60/816,117, filed on Jun. 22, 2006, provisional application No. 60/853,962, filed on Oct. 24, 2006.

(51) Int. Cl.
*A61B 17/58* (2006.01)
(52) U.S. Cl. .................. 606/86 A; 606/151; 606/99
(58) Field of Classification Search .................. 606/248, 606/206, 207, 208, 209, 210, 211, 246, 280, 606/96, 89, 94, 86 A, 250, 151, 92, 99; 128/898
See application file for complete search history.

(56) References Cited

U.S. PATENT DOCUMENTS

| | | | | |
|---|---|---|---|---|
| 887,103 A | * | 5/1908 | Lane | ........................ 269/156 |
| 2,416,228 A | * | 2/1947 | Sheppard | .................... 408/105 |
| 2,757,665 A | * | 8/1956 | Tanikawa | ............... 606/204.45 |
| 3,906,957 A | | 9/1975 | Weston | |
| 4,246,895 A | * | 1/1981 | Rehder | ........................ 606/89 |
| 4,896,663 A | * | 1/1990 | Vandewalls | .................. 606/79 |
| 5,464,413 A | * | 11/1995 | Siska et al. | ................. 606/151 |
| 6,048,346 A | | 4/2000 | Reiley et al. | |
| 6,066,102 A | | 5/2000 | Townsend et al. | |
| 6,277,123 B1 | | 8/2001 | Maroney et al. | |
| 6,436,117 B1 | | 8/2002 | Waller et al. | |
| 6,676,664 B1 | | 1/2004 | Al-Assir | |
| 6,773,437 B2 | | 8/2004 | Ogilvie et al. | |
| 7,611,526 B2 | * | 11/2009 | Carl et al. | .................... 606/248 |

OTHER PUBLICATIONS

European Patent Office, "Notification of Transmittal of the International Search Report and The Written Opinion of the International Searching Authority, or the Declaration," for PCT/US07/67789, mailed Jun. 26, 2008, 7 pages.

* cited by examiner

*Primary Examiner*—Pedro Philogene
(74) *Attorney, Agent, or Firm*—Haynes and Boone, LLP

(57) ABSTRACT

Systems, procedures and tools for repairing, or reinforcing the spinous process. The systems and procedures provide for injecting bone cement into and optionally around the spinous process. Additional reinforcing elements may be embedded in the bone cement inside or outside the spinous process. The procedures include positioning of the guide and reinforcing elements relative to a spinous process, preparation of the spinous process for injection and injection of bone cement into the spinous process. Tools are provided to facilitate the accurate injection of bone cement. The systems and procedures increase the strength of the spinous process and enhance the applicability and outcome of spinal interventions.

31 Claims, 14 Drawing Sheets

FIG. 7A
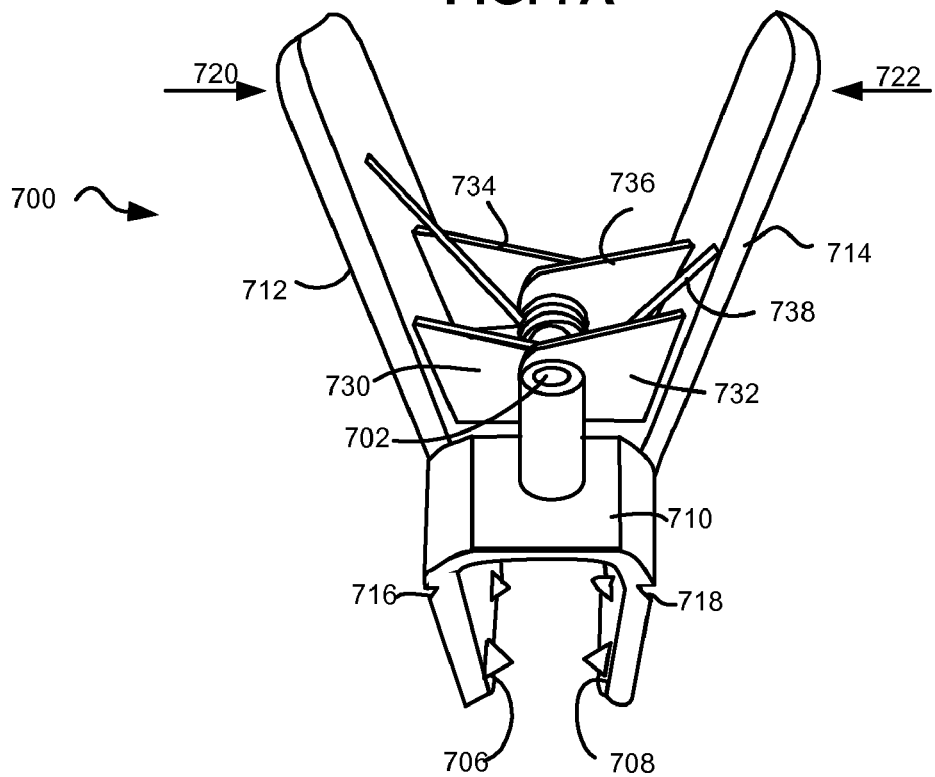
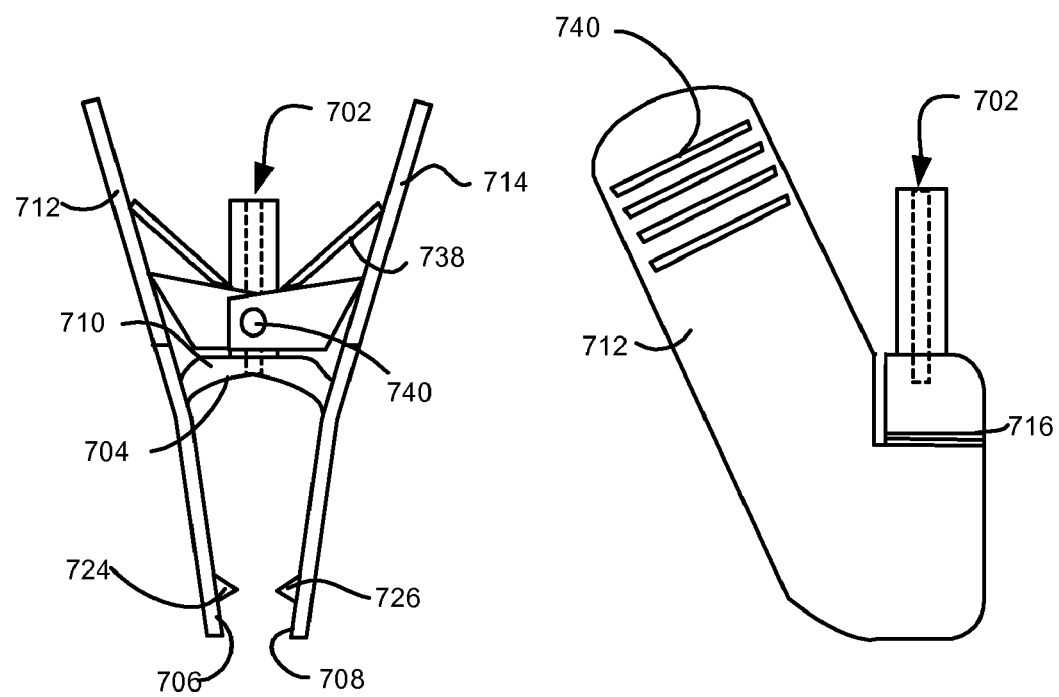
FIG. 7B  FIG. 7C

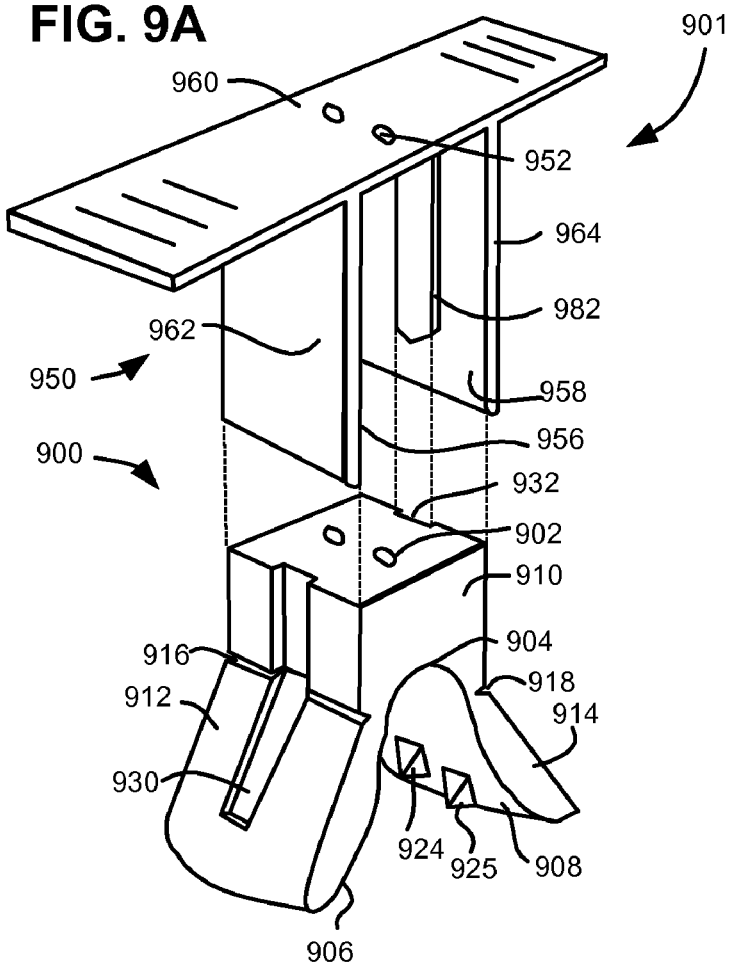
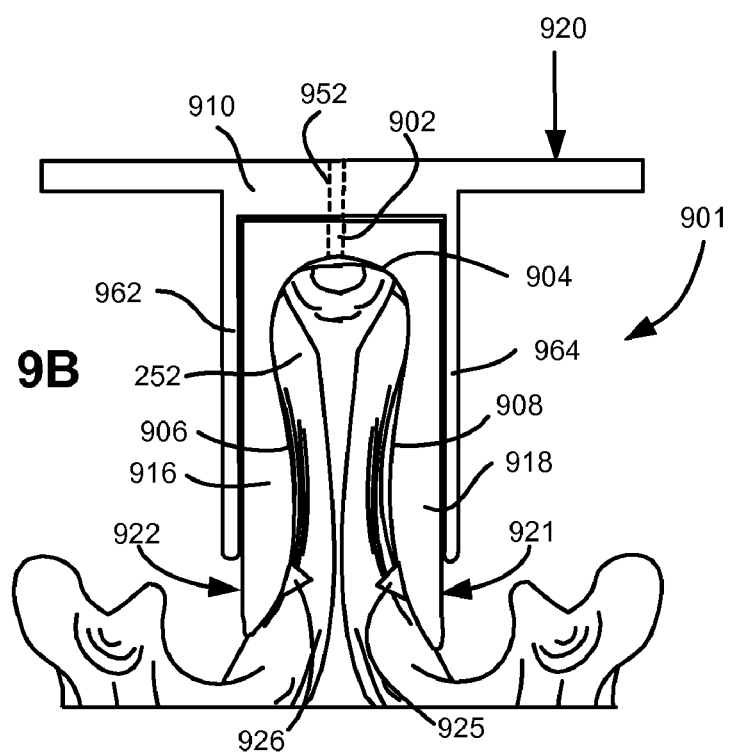

SYSTEM AND METHOD FOR STRENGTHENING A SPINOUS PROCESS

CLAIM OF PRIORITY

This U.S. Patent Application claims priority from U.S. Provisional Patent Application No. 60/816,117, filed Jun. 22, 2006 and U.S. Provisional Patent Application No. 60/853,962, filed Oct. 24, 2006, both of which are incorporated herein by reference.

BACKGROUND OF INVENTION

The spinal column has many functions including supporting the body, weight transfer and motion, and protection of the spinal cord and the nerve roots. The spinal column is a structure composed primarily of bones, ligaments, muscles, and cartilage. The bones of the spinal column are called vertebrae.

Normal healthy bone is composed of a framework made of proteins, collagen and calcium salts. Healthy bone is typically strong enough to withstand the various stresses experienced by an individual during his or her normal daily activities, and can normally withstand much greater stresses for varying lengths of time before failing. However, osteoporosis or a host of other diseases can affect and significantly weaken healthy bone over time. In osteoporosis, for example, bone mineral density is reduced over time leading to greater likelihood of fracture. If unchecked, such factors can degrade bone strength to a point where the bone is especially prone to fracture, collapse and/or is unable to withstand even normal daily stresses.

As the population ages, it is anticipated that there will be an increase in adverse spinal conditions which are characteristic of weakened bone. Also, with aging come increases in spinal stenosis, which is characterized by thickening of the bones, which make up the spinal column and facet arthropathy. These degenerative conditions as well as physical trauma can lead to failure of instability of the spinal column. Damage to the spinal column often leads to pain and difficulties with mobility. Accordingly, there surgical procedures and implants have been developed to alleviate conditions such as spinal stenosis, vertebral fracture and other spinal injury.

Many surgical interventions depend upon implanting components relative to the spinous process of the vertebra. For example, U.S. Pat. No. 6,669,842 to Zucherman et al. entitled, "Spine Distraction Implant," describes, "An implant that is implanted between adjacent spinous processes for the relief of pain associated with the spine." This device can be used to ease the pain associated with spinal stenosis. As shown in FIG. 1, an implant 101 is positioned between adjacent spinous processes 102, 103. Implant 101 comprises a spacer which is held in position between the adjacent spinous processes and increases the distance between the spinous processes thereby limiting flexion of the spine. This increases the foraminal space and relieves pressure on nerves caused by spinal stenosis and the pain caused thereby. This figure illustrates one of many spinal interventions which interact with the spinous process. U.S. Pat. No. 6,669,842 is incorporated herein by reference.

Other interventions implant components that rely for their operation upon interaction with the spinous process. However, the strength of the spinous process may have been compromised by the degenerative processes described above.

In view of the need for a strong spinous process, it would therefore be desirable to have a procedure for enhancing the strength of a spinous process of a patient.

It would also be desirable to have a minimally-invasive procedure for enhancing the strength of a spinous process of a patient.

It would further be desirable to have a procedure for enhancing the strength of a spinous process of a patient that could be performed in conjunction with a surgical intervention that affects the spinous process.

It would still further be desirable to provide tools and instruments to facilitate a procedure for enhancing the strength of a spinous process of a patient.

BRIEF DESCRIPTION OF THE DRAWINGS

The features of the invention, its nature and various advantages will be apparent from the accompanying drawings and the following detailed description of the preferred embodiments, in which:

FIG. 7A shows a perspective view of an guide in accordance with one embodiment of the present invention;

FIG. 7B shows an end view of the guide of FIG. 7A;

FIG. 7C shows a side view of the guide of FIG. 7A;

FIG. 9A shows a plan view of an guide in accordance with one embodiment of the present invention;

FIG. 9B shows a plan view of the guide of FIG. 9A in the deployed configuration;

DETAILED DESCRIPTION OF THE INVENTION

Figure 1:
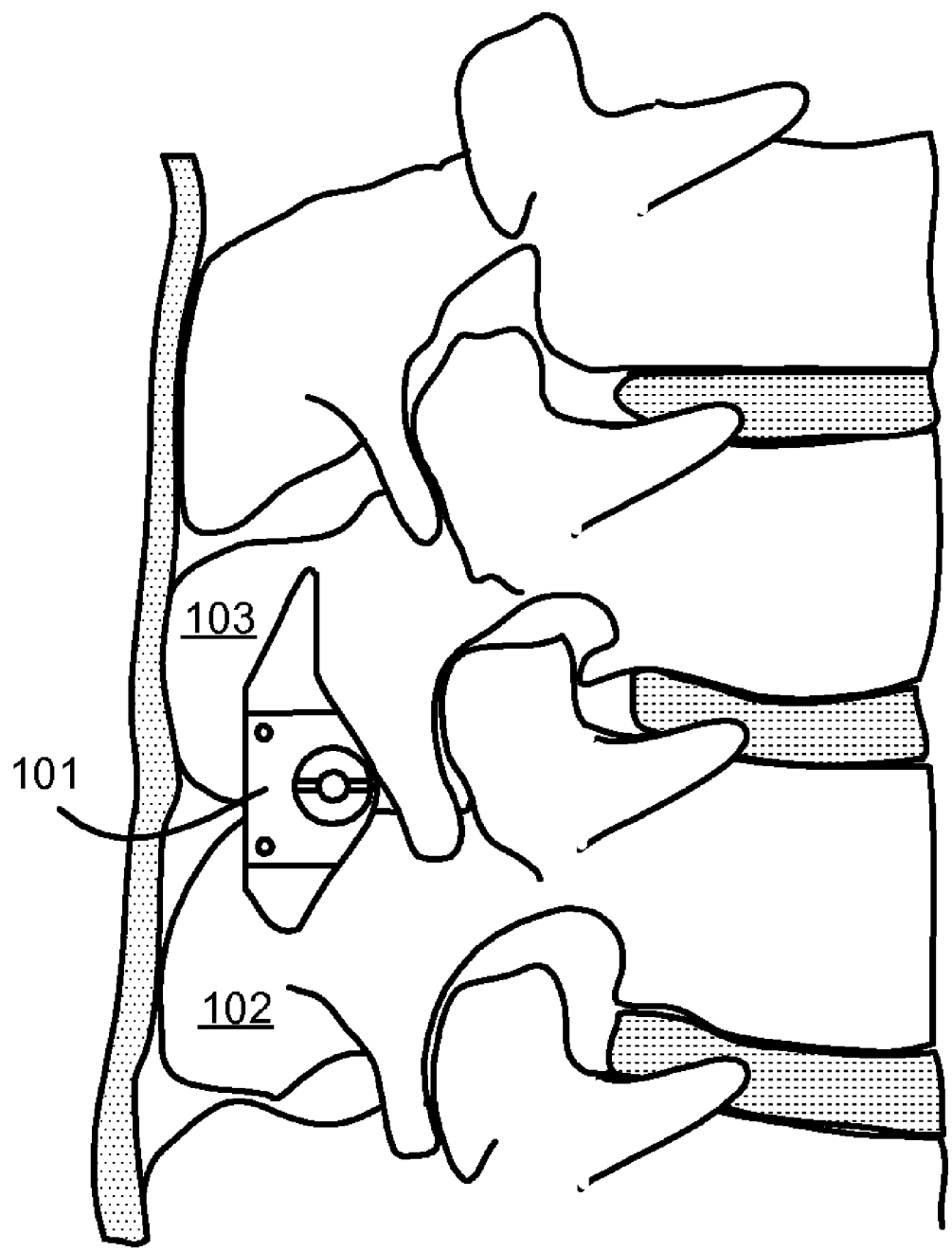
FIG. 1 shows a surgical implant in position between adjacent spinous processes.

In view of the foregoing background of the invention, it is an object of the present invention to provide a procedure for enhancing the strength of a spinous process of a patient.

It is also an object of the present invention to provide a minimally-invasive procedure for enhancing the strength of a spinous process of a patient.

It is a further object of the present invention to provide a procedure for enhancing the strength of a spinous process of a patient that may be performed in conjunction with a surgical intervention that affects the spinous process.

It is still further an object of the present invention to provide tools and instruments to facilitate a procedure for enhancing the strength of a spinous process of a patient.

These and other objects of the present invention are accomplished by injecting a flowable bone filler, such as polymethylmethacrylate (PMMA—commonly known as bone cement), into a fractured, weak, or diseased spinous process and lamina. Shortly after injection, the liquid bone cement material hardens or polymerizes, desirably supporting the spinous process and lamina internally. The procedure may make use of a guide element and corresponding tools to assist and control the injection of the flowable bone cement into and optionally around the spinous process.

In a general embodiment of the present invention, an insertion device, such as a needle, is inserted into a targeted spinous process using a guide to control the positioning of the needle and the depth of insertion. A bone filler such as bone cement is injected through the needle into the spinous process. Bone cement introduction is halted and the needle is retracted as a desired fill amount is reached. The bone cement is then allowed to harden.

In an alternative embodiment of the present invention, one or more reinforcing elements are introduced into or around the spinous process. The reinforcing elements may be in the form of, for example, mesh, wire, pins, needles or clips. In one embodiment, reinforcement is provided by utilizing a titanium needle for injection of bone cement and leaving a portion of the needle implanted in the spinous process.

Additional objects, advantages, and embodiments of the invention are set forth in part in the description which follows, and in part, will be obvious from this description, or may be learned from the practice of the invention. The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the left-most digit of a reference number identifies the drawing in which the reference number first appears.

Injection of Bone Cement

Figure 2A:
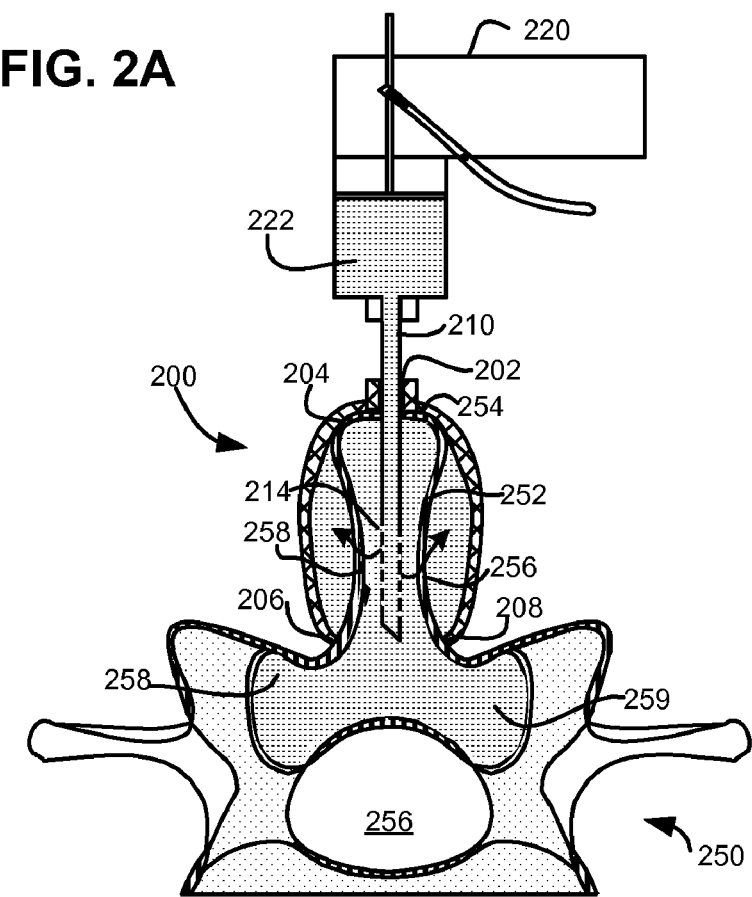
FIG. 2A shows a sectional view of a guide, needle and a bone cement injector engaged with the spinous process of a vertebra in accordance with one embodiment of the invention.

Referring now to FIG. 2A which shows a sectional view of a guide 200 engaged with a spinous process 252 of a vertebra 250. Guide 200 defines a bore or guide bore 202. Bore 202 is aligned with the center of spinous process 252 and the axis of bore 202 is aligned with the axis of spinous process 252. Guide 200 comprises one apex engagement surface 204 to engage the apex 254 of spinous process 252. Guide 200 further comprises two lateral engagement surfaces 206, 208 to engage the lateral sides 256, 258 of spinous process 252. Lateral engagement surfaces 206, 208 align the axis of guide 200 with the axis of spinous process 252.

Figure 2B:
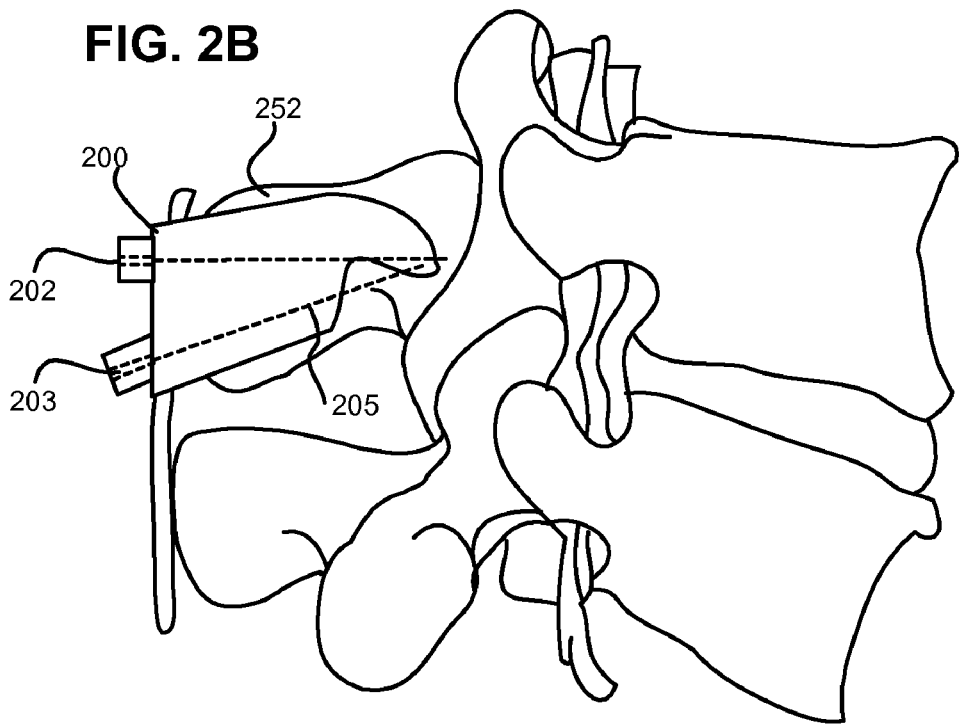
FIG. 2B shows a lateral view of the guide of FIG. 2A.

A guide may be provided with multiple guide bores to direct injection at multiple points in the spinous process. In a preferred embodiment the guide comprises guide bore 202 and a second guide bore 203 as shown in FIG. 2B. The axis of each guide bore is aligned with the axis of the spinal process which is in the midline between the lateral sides of the spinous process 252. Some spinous processes are angled in the vertical plane. Thus, the axis of a guide bore may be angled cranially or ventrally to ensure that insertion of the needle is along a path within the spinous process. As shown in FIG. 2B the axis of guide bore 202 is horizontal and the axis of guide bore 203 is angled cranially so as to maintain needle trajectory 205 within spinous process 252.

As shown in FIG. 2A, a needle 210 is inserted through bore 202 of guide 200 into spinous process 252. Guide bore 202 constrains the range of motion of needle 210 such that it can only be inserted along the central axis of the spinous process 252. Guide 200 thus ensures that needle 210 penetrates the cortical bone at the center of the apex of spinous process 252 and passes through cancellous bone through the middle of spinous process 252.

During insertion, the physician must take care that needle 210 does not enter spinal canal 256. Thus, it is preferred that the needle depth be mechanically limited to prevent insertion into spinal canal 256. Preferably the needle is constructed such that it engages the guide to prevent further insertion at a maximum insertion depth that is less than depth of insertion required to enter the spinal canal. The needle will preferably by inserted to a depth of from 50 percent to 95 percent of the distance from the apex of the spinous process to the wall of the spinal canal. More, preferably, needle 210 and guide 200 are designed such that tip 212 of needle 210 at its maximal insertion is within the boundary area between the lamina and the spinous process.

Typically, needle 210 is introduced into spinous process 252 under X-ray control or a similar visualization system. The visualization system may also be used to determine proper placement of guide 200. Guide 200 may be made of metal and visible under X-ray. If guide 200, is made of polymer material, it may be impregnated with radio-opaque material or have radio-opaque markers applied to the guide surface to allow X-ray visualization. The visualization system may also be used to monitor injection of bone cement 222. Bone cement 222 typically includes radio-opaque materials in order to facilitate visualization of the bone cement.

As shown in FIG. 2A, needle 210 is attached to bone cement injection device 220. Needle 210 may be provided with a threaded bore, luer lock, or similar coupling which mates with a bone cement injection device for this purpose. The bone cement injection device may be a syringe or similar device. However, several companies offer purpose-made bone cement injection devices. A typical injection device has a pistol-shaped body, which supports a cartridge containing bone cement. The cement is typically in two-parts and must be mixed in a mixer and transferred into the cartridge for injection. Just after mixing, and prior to curing, the cement is in a flowing, viscous liquid state. The injection device has a ram, which is actuated by a manually movable trigger or screwing mechanism for pushing the viscous bone cement out the front of the cartirdge through a suitable nozzle and into the interior of a bone. One suitable injection device is made by Stryker Corporation (Kalamazoo, Mich.) for example. This gun is manually operated tough other types of injection device may be used including non-manual injection devices. Further description of commercially available bone cement and bone cement mixing and injection devices is provided below.

As shown in FIG. 2A, injection device 220 forces bone cement 222 along needle 210 into spinous process 252. The bone cement will flow into lamina 258, 259. Needle 210 may be inserted or withdrawn from the spinous process during injection of bone cement such that bone cement 222 is injected at different points in spinous process 252. This allows optimal impregnation of spinous process 252 with bone cement 222. In addition, the needle may be provided with one or more side ports 214 as shown in FIG. 2, instead of or in addition to the opening at the tip of the needle. The side ports 214 allow for outflow of bone cement 222 and impregnation of the spinous process 252 along the length of the needle 210. The physician may monitor injection of the bone cement fluoroscopically and/or by direct visual observation if permitted by exposure of the spinous process.

Bone cement 222 undergoes a curing cycle of approximately 6 to 12 minutes. While curing, the cement passes from a viscous liquid to a hard rigid block. The bone cement must be injected and the needle withdrawn (if it is to be withdrawn) prior to hardening of the bone cement. After bone cement 222 has hardened, guide 200 may be removed from the spinous process. In order to reduce the possibility of guide 200 being stuck to spinous process 252, guide 200 may be provided with a coating of a non-stick material such as TEFLON™ on any surface that comes in contact with the bone cement or spinous process. Alternatively, the portions of guide 200 that are exposed to the bone cement or spinous process, or indeed the entire guide, may be made from a non-stick plastic polymer such as TEFLON™.

In certain cases, it may be desirable to deposit bone cement 222 around the spinous process 252 in order to further strengthen the spinous process 252. In such cases, guide 200 may be used to control the location and shape of bone cement 222 surrounding the spinous process 252. In this procedure, the guide 200 is placed over the spinous process 252 and then sealed to the spinous process 252. A needle 210 is then inserted into the spinous process 252 and bone cement 222 injected. Bone cement injection is continued until all fissures in the spinous process 252 have been filled and bone cement 222 has filled any space between the spinous process 252 and guide 200. To assist flow of bone cement 222 from the spinous process 252 into the area between the spinous process 252 and guide 200, the sides of the spinous process 252 may be perforated with a needle or similar instrument prior to location of the guide. The perforations facilitate the flow of bone cement 222 into the space between the guide 200 and the spinous process 242. After injection, the bone cement 222 is allowed to cure. The guide 200 controls the position of bone cement 222 during curing and may be removed after the bone cement 222 has hardened. To aid removal, the guide may be coated with TEFLON™ or similar non-stick material.

Reinforcing Elements

FIGS. 3A-C and 4A-B illustrate the application of reinforcing elements to the exterior of a spinous process in conjunction with the injection of bone cement in accordance with embodiments of the present invention. Exterior reinforcing elements are structural elements that are positioned close to and/or around the spinous process and which are adhered to and/or embedded in the bone cement to reinforce the bone cement. Exterior reinforcing elements may include, for example, meshes, wires, clips, strands, fibers and the like. The surface of the exterior reinforcing elements is preferably designed and/or selected to promote adhesion by the bone cement.

Figure 3A:
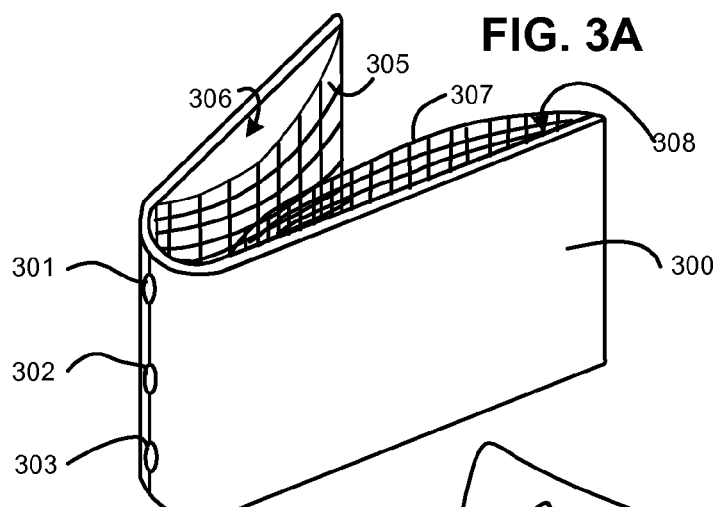
FIG. 3A shows a perspective view of a guide provided with mesh reinforcing elements in accordance with one embodiment of the present invention.

FIG. 3A illustrates a guide 300 having three guide bores 301, 302, 303 for guiding the insertion of a needle or needles 210 into a spinous process. Also, as shown in FIG. 3A, guide 300 is provided with two exterior reinforcing elements 305, 307, which in this example comprise sections of a mesh disposed over the lateral engagement surfaces 306, 308 of guide 300. A suitable mesh for use as an exterior reinforcing element may comprise a deformable metal wire mesh made from an implantable metal such as titanium or stainless steel or a biocompatible non-metallic mesh such as glass fiber, carbon fiber or a biocompatible polymer. One commercially-available implantable titanium mesh is CYTOFLEX® Mesh from Unicare Biomedical, Inc. of Laguna Hills, Calif.

Figure 3B:
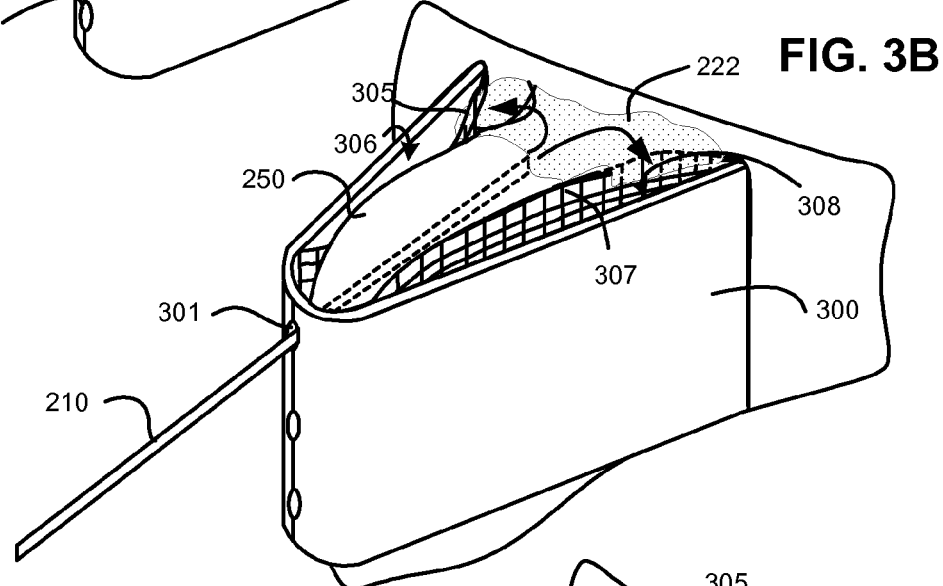
FIG. 3B shows a perspective view of the guide and reinforcing elements of FIG. 3A in position over a spinous process during injection of bone cement.
Figure 3C:
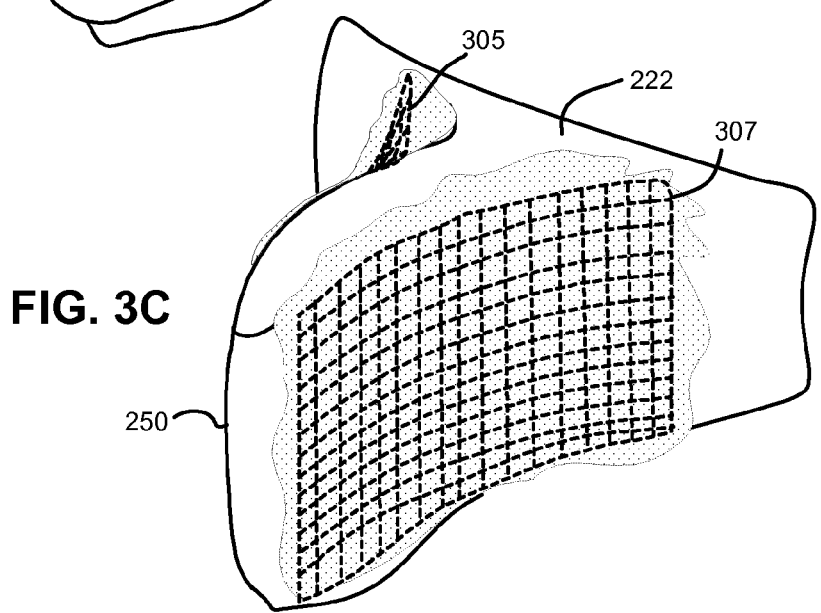
FIG. 3C shows a perspective view of the spinous process and reinforcing elements of FIG. 3B after the guide has been removed.

As shown in FIG. 3B, when guide 300 is placed over spinous process 252, the two exterior reinforcing elements 305, 307 are positioned between lateral engagement surfaces 306, 308 and spinous process 252. The exterior reinforcing elements 305, 307 are urged into contact with the surface of spinous process 252. As shown in FIG. 3B, as bone cement 222 is injected through needle 210 into spinous process 252, some bone cement 222 seeps into the space between guide 300 and spinous process 252. Bone cement 222 seeps through and around exterior reinforcing elements 305, 307 such that exterior reinforcing elements 305, 307 become embedded in bone cement 222. The bone cement 222 may also be directed into any voids between spinous process 252 and guide 300 by positioning the tip of a needle in the void and injecting bone cement directly into the void. The guide may be provided with side ports to provide access to any voids between the guide and the lateral surfaces of the spinous process. After bone cement 222 has cured, guide 300 may be removed. As illustrated in FIG. 3C, the two exterior reinforcing elements 305, 307, remain embedded in bone cement 222 and attached to spinous process 252 when guide 300 has been removed. The surface texture of the mesh is preferably selected to promote adhesion to the bone cement. The two exterior reinforcing elements 305, 307 impart additional strength to the bone cement in which they are embedded and thus to spinous process 252.

Figure 4A:
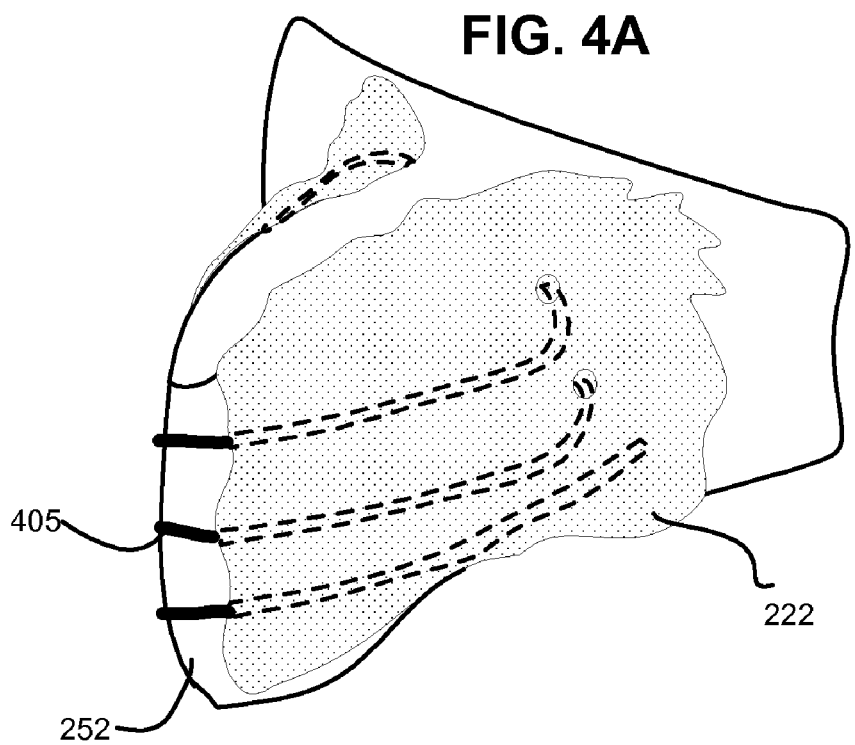
FIG. 4A shows a perspective view of a spinous process with wire reinforcing elements in accordance with one embodiment of the present invention.

FIG. 4A illustrates an alternative exterior reinforcing element which may be used in combination with bone cement 222 to strengthen a spinous process 252. As shown in FIG. 4A, a wire 405 or combination of wires of a suitable implantable metal such as stainless steel or titanium may be wrapped around and optionally through spinous process 252 prior to placement of a guide 300. When the guide is removed after injection of the bone cement, wire 405 remains embedded in bone cement 222. Wire 405 imparts additional strength to bone cement 222 and consequently to spinous process 222.

Wire 405 may optionally pass through spinous process 252 as shown in FIG. 4A to provide additional anchorage and support to spinous process 252.

Figure 4B:
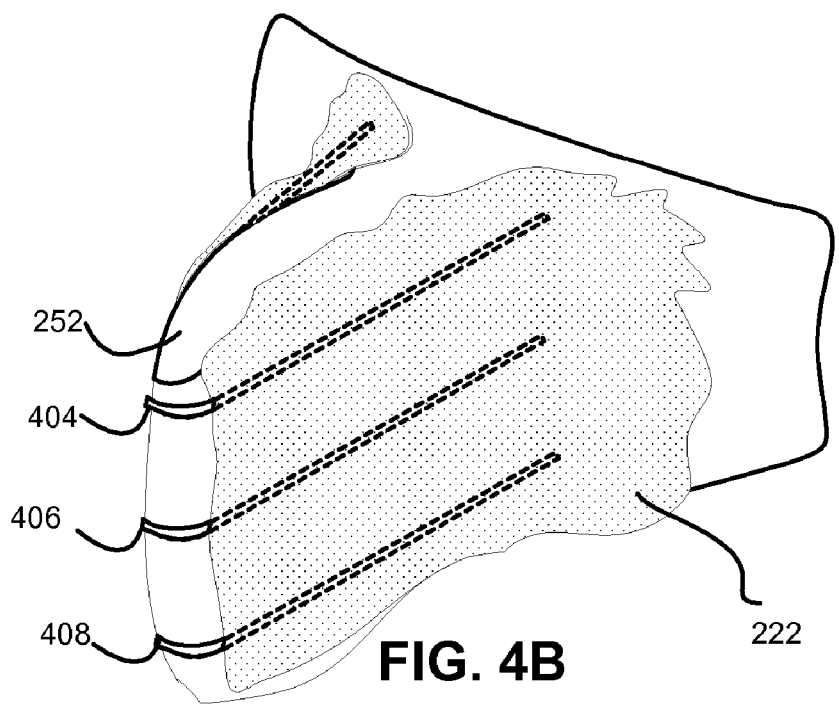
FIG. 4B shows a perspective view of a spinous process with clip reinforcing elements in accordance with one embodiment of the present invention.

FIG. 4B illustrates another alternative exterior reinforcing element which may be used in combination with bone cement 222 to strengthen a spinous process 252. As shown in FIG. 4B, clips 404, 406, 408 may also be used as exterior reinforcing elements. Clips 404, 406, 408 may be placed over spinous process 252 prior to placement of a guide or at the same time as placement of guide (by using the same method demonstrated with respect to the exterior reinforcing elements of FIGS. 3A-B). When the guide is removed after injection of the bone cement, clips 404, 406, 408 remain embedded in bone cement 222. Clips 404, 406, 408 impart additional strength to bone cement 222 and consequently to spinous process 252. Clips 404, 406, 408 may optionally penetrate spinous process 252 or lamina 258, 259 to provide additional anchorage and support to spinous process 252.

Figure 4C:
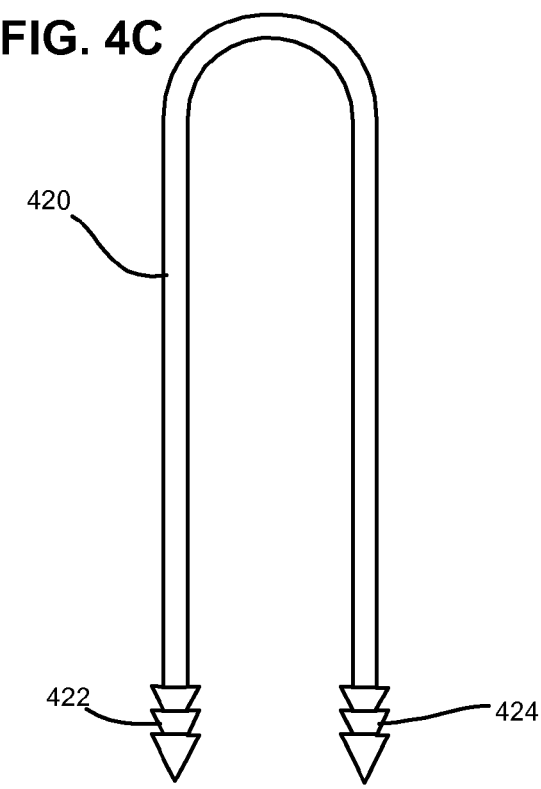
FIG. 4C shows a plan view of a clip reinforcing element in accordance with one embodiment of the present invention.
Figure 4D:
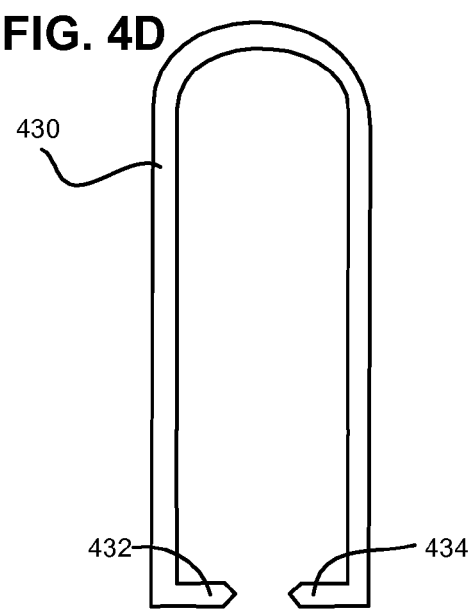
FIG. 4D shows a plan view of a clip reinforcing element in accordance with one embodiment of the present invention.
Figure 4E:
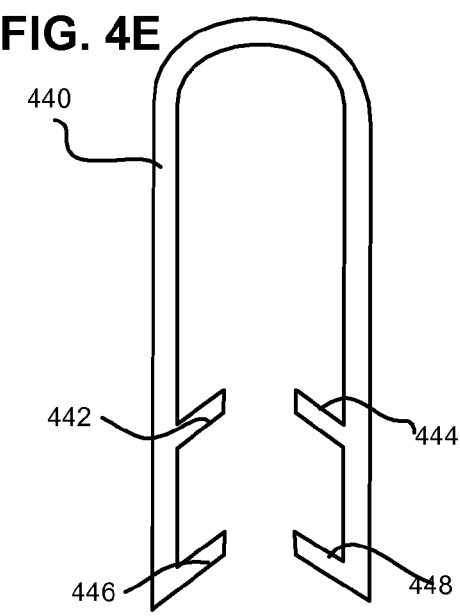
FIG. 4E shows a plan view of a clip reinforcing element in accordance with one embodiment of the present invention.

FIGS. 4C-D show different clips that may be deployed as shown in FIG. 4B. As shown in FIG. 4C, a clip 420 may comprise barbed tips 422, 424. Clip 420 is sized such that, when positioned over a spinous process, barbed tips 422, 424 enter the lamina on either side of the spinous process, anchoring the clip in position. As shown in FIG. 4D, a clip 430 may comprise pointed distal tips 432, 434 turned towards the spinous process. Clip 430 is sized such that, when positioned over a spinous process, distal tips 432, 434 engage the lateral surfaces of the spinous process, anchoring the clip into position. As shown in FIG. 4E, a clip 440 may comprise restraining fingers 432, 434, 436, 438 turned towards the spinous process. Clip 440 is sized such that, when positioned over a spinous process, restraining fingers 432, 434, 436, 438 make contact with the lateral surfaces of the spinous process. The restraining fingers are angled backwards from the distal end of the clip towards the proximal end such that insertion over the spinous process is facilitated. The restraining fingers engage the lateral surfaces of the spinous process, anchoring the clip into position. The clips of FIGS. 4B-E may be constructed of an implantable metal, such as stainless steel or titanium, or suitable implantable non-metallic materials.

Figure 5A:
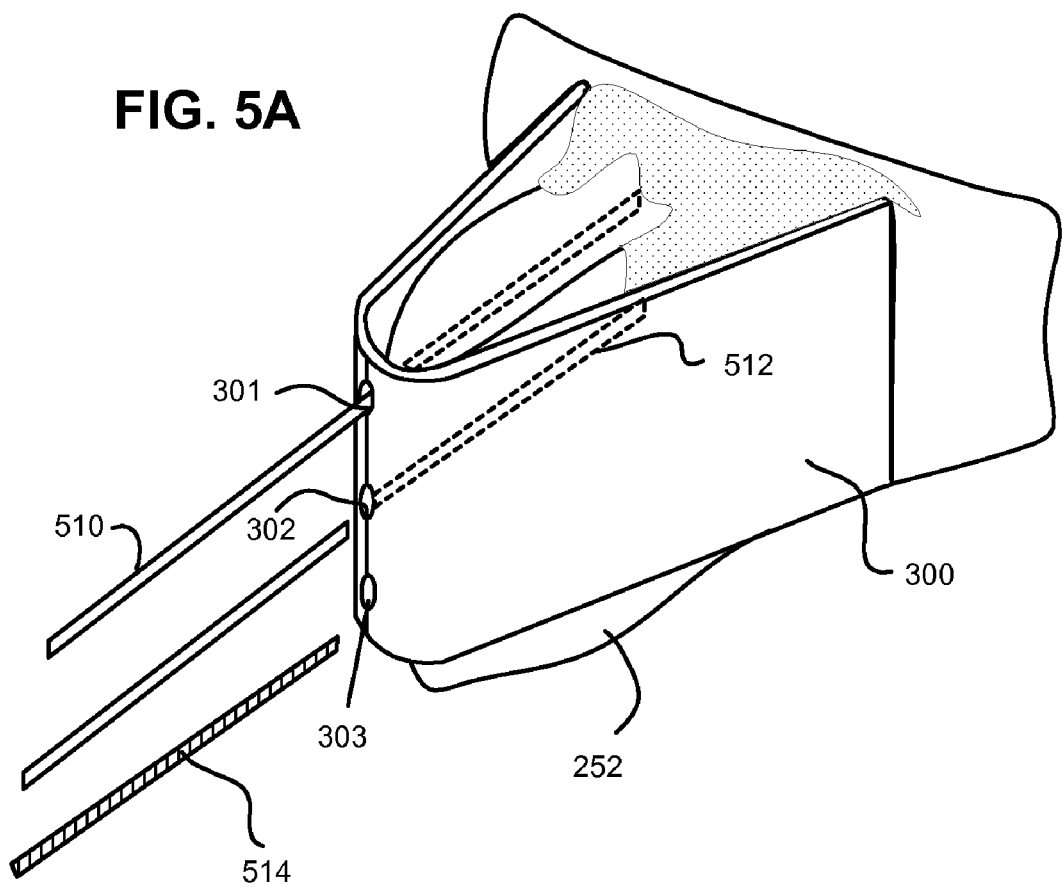
FIG. 5A shows a perspective view of a guide and spinous process with needle reinforcing elements in accordance with one embodiment of the present invention.
Figure 5B:
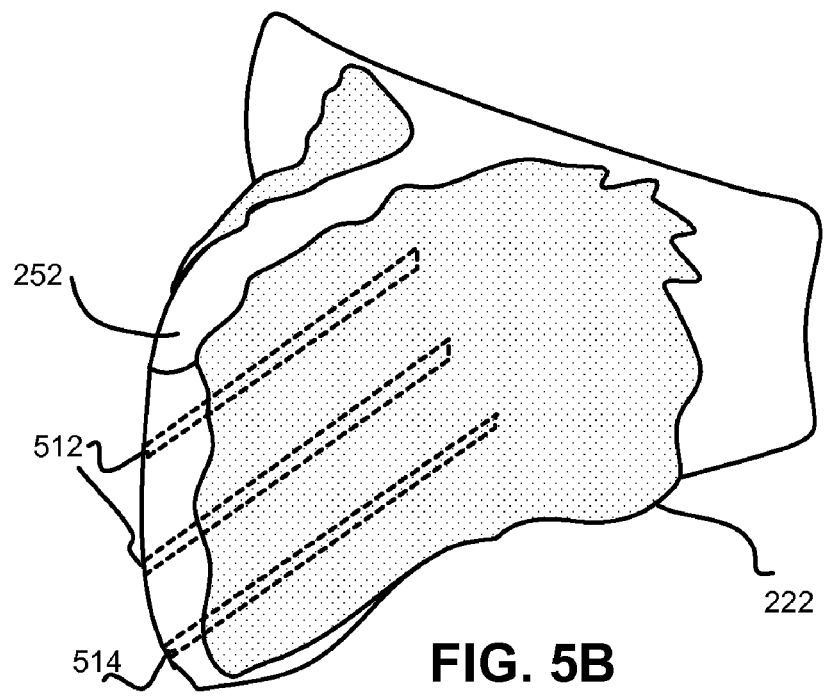
FIG. 5B shows a perspective view of the spinous process with needle reinforcing elements of FIG. 5A after removal of the guide.

FIGS. 5A-B illustrate the application of reinforcing elements to the interior of a spinous process in conjunction with the injection of bone cement in accordance with certain embodiments of the present invention. Interior reinforcing elements are structural elements that are positioned inside the spinous process and which are adhered to and/or embedded in the bone cement to reinforce the bone cement. Interior reinforcing elements may include, for example, needles, pins, wires, rods screws nails and the like. The surface of the interior reinforcing, elements is preferably designed and/or selected to promote adhesion by the bone cement.

As shown in FIG. 5A, guide 300 has three guide bores 301, 302, 303. A needle 510 for injection of bone cement 222 is shown inserted in guide bore 301. After injection of bone cement 222, needle 510 may be cut or snapped close to the apex of spinous process 252 leaving a portion 512 of the needle embedded inside the spinous process in the bone cement (as shown at guide bore 302). In an alternative, procedure, needle 510 may be removed from the spinous process 252 after injection of bone cement 222 and a separate reinforcing element comprising a pin or screw 514 may be inserted through the guide bore into the spinous process prior to curing of the bone cement (as shown at guide bore 303). To serve as a reinforcing element in spinous process 252), the needle 510 or pin 514 should be made of a strong implantable material such as titanium or surgical stainless steel. As shown in FIG. 5B portions 512 of needles 510, and the entirety of pin or screw 514 remain embedded in the bone cement inside the spinous process after the guide has been removed. The needles, pins or screws embedded inside the spinal process function as interior reinforcing elements which impart additional strength to the spinous process. Interior reinforcing elements may be used alone or in conjunction with the exterior reinforcing elements described above.

Bone Cement Injection Guides

As described above with respect to FIGS. 2A-B. In embodiments of this invention, a guide may be used to facilitate accurate insertion of a needle into a spinous process for injection of bone cement. In some embodiments of the present invention, a surgeon may inject bone cement into a spinous process without a using a guide to control the needle. However, if a guide is used, the guide can be designed to control the point of insertion of the needle or instrument into the spinous process, the axis of insertion of the needle or instrument through the spinous process and the maximum depth of insertion of the needle or instrument into the spinous process. A guide can also function to control the location of bone cement and exterior reinforcing elements. FIGS. 6A-C, 7A-C, 8A-B, 9A-B, 10A-B, 11A-B, 12A-B AND 13A-B illustrate bone cement injection guides in accordance with various embodiments of the present invention.

Figure 6A:
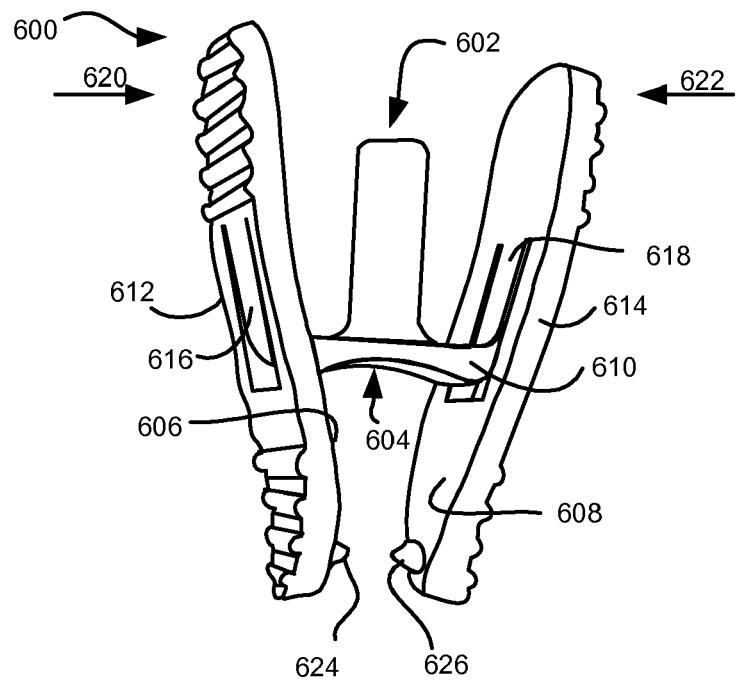
FIG. 6A shows a perspective view of a guide in accordance with one embodiment of the present invention.
Figure 6B:
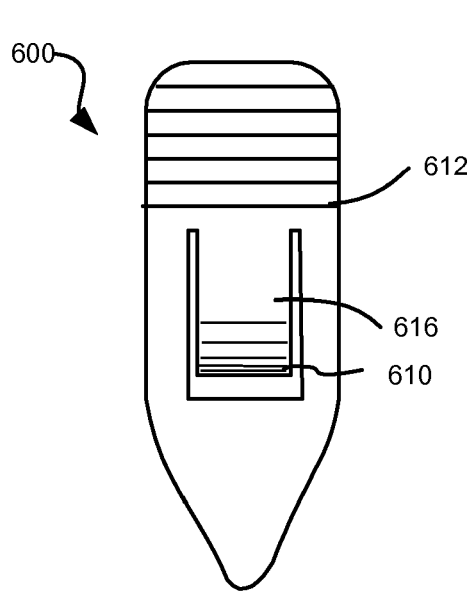
FIG. 6B shows a side view of the guide of FIG. 6A.
Figure 6C:
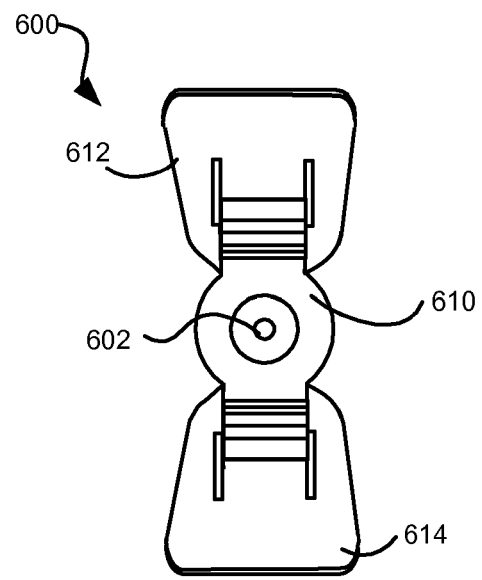
FIG. 6C shows an overhead view of the guide of FIG. 6A.

FIGS. 6A-C illustrate three views of an embodiment of a guide in accordance with an embodiment of the present invention. FIG. 6A shows a perspective view of a generally H-shaped guide 600 having a guide bore 602 in connector 604. Connector 610 comprises a curved apex engagement surface 604 for engaging the apex of a spinous process. Guide bore 602 acts as a position and direction guide for introduction of a needle or other surgical instrument. Guide 600 may also act as a depth guide to limit the depth of insertion of a needle or other instrument into a spinous process.

Guide 600 comprises two arms 612, 614 which extend above and below connector 610. Arms 612, 614 are sized such they contact the lamina on either side of a spinous process or contact the lateral surfaces of the spinous process. As shown in FIG. 6A, arms 612, 614 have a slight S-shaped curve. As shown in FIG. 6B, arms 612, 614 are also tapered distal of connector 610 for ease of insertion over a spinous process. In this embodiment, arms 612, 614 are formed in one piece with connector 610. The connections between connector 610 and arms 612, 614 comprise two living hinges 616, 618. The living hinges 616, 618 allow the distal portions of arms 612, 614 to flex away from each other when pressure is applied as shown by arrows 620, 622 to the portion of arms 612, 614 proximal to connector 604.

Arms 612, 614 comprise curved lateral engagement surfaces 606, 608 distal of connector 610. The lateral engagement surfaces are designed to engage the spinous process while centering guide bore 602 on the apex of the spinous process. Lateral engagement surfaces 606, 608 are provided with gripping elements 624, 626 to better grip the spinous process. In this embodiment, gripping elements 624, 626 comprise conical spikes formed on lateral engagement surfaces 606, 608. In an unflexed configuration of guide 600, lateral engagement surfaces 606, 608 are closer together than the width of the apex of a spinous process and the sides of a spinous process. When forces are applied to the portions of arms 612, 614 proximal to connector 610, the space between lateral engagements surfaces 606, 608 is increased allowing guide 600 to be positioned over the spinous process with apex engagement surface 604 in contact with the apex of the spinous process. When the forces are removed, guide 600 returns towards its unflexed position until lateral engagement surfaces 606, 608 come into contact with spinous process 252. Tension remaining in guide 600 continues to press lateral engagement surfaces 606, 608 and gripping elements 624, 626 into the sides of spinous process 252 thereby securing guide 600 to spinous process 252.

FIGS. 7A-C illustrate three views of another embodiment of a guide in accordance with the principles of this invention for guiding insertion of a needle into a spinous process. FIG. 7A shows a perspective view of an H-shaped guide 700 having a guide bore 702 in connector 710. Connector 710 comprises a curved apex engagement surface 704 for engaging the apex of a spinous process. Guide 700 acts as a position and direction guide for introduction of a needle or other surgical instrument. Guide 700 may also serve as a depth guide to limit the depth of insertion of a needle or surgical instrument into a spinous process.

Guide 700 comprises two arms 712, 714 which extend above and below connector 710. Arms 712, 714 may be sized such they contact the lamina or lateral surfaces on either side of a spinous process to be reinforced. As shown in FIG. 7A, arms 712, 714 may have a shallow V-shape but may alternatively be straight or have a shallow S-shape (as illustrated in FIGS. 6A-C, above). As shown in FIG. 7B arms 712, 714 are tapered distal of connector 710 for ease of insertion over a spinous process 252. In this embodiment, arms 712, 714 are formed in one piece with connector 702 which is disposed between them. Alternatively, arms 712, 714 and connector 710 may be formed as separate components which are subsequently assembled. In this embodiment, the connections between connector 710 and arms 712, 714 comprise two living hinges 716, 718. The living hinges 716, 718 allow the distal portions of arms 712, 714 to flex away from each other while maintaining the axis of guide bore 702 along the center line of a spinous process. An alternative embodiment can be provided where the living hinges 716, 718 are eliminated. Connector 710 is, in this embodiment, sufficiently flexible to allow motion of arms 712, 714 while maintaining the position and orientation of guide bore 702. Arms 712, 714 are also provided with attachment lugs 730, 732, 734, 736. A shaft 740 is used to connect the lugs and a spring 740 is mounted on the shaft. Spring 740 pushes outwards against the portions of arms 712, 714 proximal to connector 710. Spring 740 thus urges the distal portion of arm 712 towards the distal portion of arm 714.

Arms 712, 714 include lateral engagement surfaces 706, 708 distal of connector 710 to engage the spinous process while centering guide bore 702 on the apex of the spinous process. Lateral engagement surfaces 706, 708 are provided with gripping elements 724, 726 to secure the guide 700 to a spinous process. Gripping, elements 724, 726 may comprise conical spikes (as shown), spikes or other protrusions formed on lateral engagement surfaces 706, 708. In an unflexed configuration, lateral engagement surfaces 706, 708 are closer together than the width of the apex of a spinous process and the sides of a spinous process. When forces are applied to the portions of arms 712, 714 proximal to connector 710, the space between lateral engagement surfaces 706, 708 is increased allowing guide 700 to be positioned over the spinous process with apex engagement surface 704 in contact width the apex of the spinous process. Note that the outside surface of the portions of arms 712, 714 proximal to connector 710 is provided with gripping features 740 such as depressions and protrusions which facilitate the gripping of guide 700 by a physician. When the forces are removed, guide 700 returns towards its unflexed position until lateral engagement surfaces 706, 708 come into contact with spinous process 252. Tension remaining in spring 740 continues to press lateral engagement surfaces 706, 708 and gripping elements 724, 726 into the sides of spinous process 252 thereby securing guide 700 to the spinous process. The spring strength and the winding tension may be adjusted as necessary to achieve the desired clamping forces.

Figure 8A:
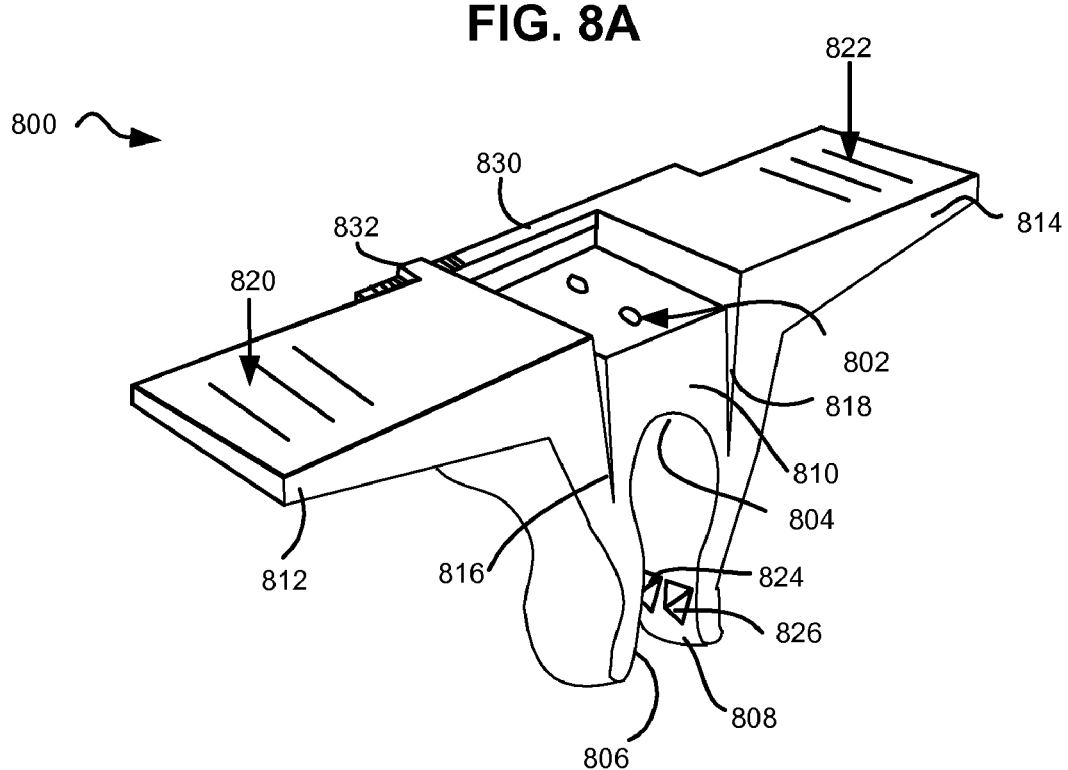
FIG. 8A shows a perspective view of an guide in accordance with one embodiment of the present invention.
Figure 8B:
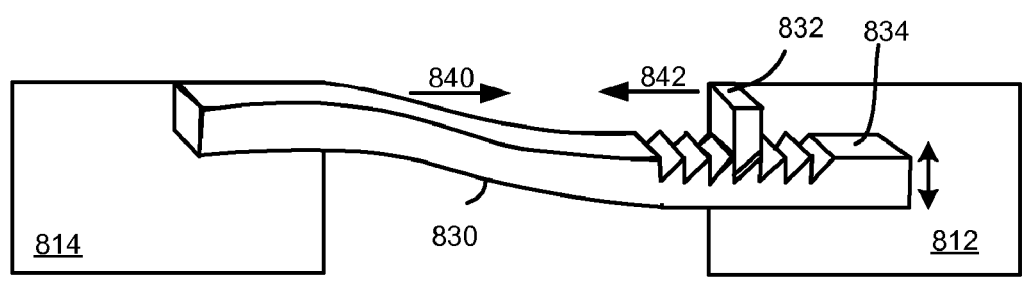
FIG. 8B shows a detailed view of the locking elements of the guide of FIG. 8A.

FIGS. 8A-B illustrate two views of another embodiment of a guide in accordance with an embodiment of the present invention. FIG. 8A shows a perspective view of a T-shaped guide 800 having a guide bore 802 in connector 810. Connector 810 comprises a curved apex engagement surface 804 for engaging the apex of a spinous process. Guide bore 802 acts as a position and direction guide for introduction of a needle or other surgical instrument. Guide 800 may also serve as a depth guide to limit the depth of insertion of a needle or surgical instrument into a spinous process.

Guide 800 comprises two L-shaped arms 812, 814 which engage the spinous process while centering guide bore 802 on the apex of the spinous process. As shown in FIG. 8B arms 812, 814 are also tapered distal of connector 810 for ease of insertion over a spinous process. Arms 812, 814 may be sized such they contact the lamina or lateral surfaces on either side of a spinous process to be reinforced. In this embodiment arms 812, 814 may be formed in one piece with connector 810 disposed between them. The connections between connector 810 and arms 812, 814 form two living hinges 816, 818. The living hinges 816, 818 allow the distal portions of arms 812, 814 to flex towards each other when pressure is applied as shown by arrows 820, 822 to the portions of arms 812, 814 proximal to connector 810.

Arms 812, 814 comprise lateral engagement surfaces 806, 808 distal of connector 810. Lateral engagement surfaces 806, 808 are provided with gripping elements 824, 826 to secure guide 800 to a spinous process. In this embodiment, gripping elements 824, 826 comprise conical spikes formed on lateral engagement surfaces 806, 808. In the unflexed configuration, lateral engagement surfaces 806, 808 are approximately the same distance apart as the width of the apex of a spinous process thereby allowing guide 800 to be positioned over a spinous process. When forces are applied to the portions of arms 812, 814 proximal to connector 810, the space between lateral engagement surfaces 806, 808 is reduced forcing them into contact with the lateral surfaces of a spinous process. The downward force shown by arrows 820 and 822 also serves to urge apex engagement surface 804 into better contact with the apex of a spinous process.

Arms 812, 814 are also provided with lock elements 830, 832. As shown in FIG. 8B, the lock elements 830, 832 comprise a ratchet and pawl mechanism which resists motion of the lock elements in the direction of arrows 840, 842. As lateral engagement surfaces 806, 808 come into contact with spinous process 252, locking elements 830 and 832 engage one another to prevent the clamping force from being released. Tension in living hinges 816, 818 presses lateral engagement surfaces 806, 808 and gripping elements 824, 826 into the sides of spinous process 252 thereby securing guide 800 in position. As shown in FIG. 8B, after injection and curing of bone cement, lock element 830 may be released by pushing down on release 834 and disengaging the surfaces of lock elements 830, 832. Such a locking mechanism may be readily incorporated into the guides of FIGS. 6A-C and 7A-C.

FIGS. 9A-B illustrate two views of another embodiment of a guide in accordance the present invention. FIG. 9A shows a perspective view of a two-component guide system 901 comprising a guide 900 and a guide tool 950. The guide 900 has a guide bore 902 in connector 910. Connector 910 also comprises a curved apex engagement surface 904 for engaging the apex of a spinous process. Guide bore 902 acts as a position and direction guide for introduction of a needle or other surgical instrument. Guide 900 may also serve as a depth guide to limit the depth of insertion of a needle or surgical instrument into a spinous process.

Guide 900 comprises two arms 912, 914 which engage the spinous process while centering guide bore 902 on the apex of the spinous process. Arms 912, 914 may be sized such they contact the lamina or lateral surfaces on either side of a spinous process. In this embodiment arms 912, 914 may be formed in one piece with connector 902 disposed between them or the arms and connector may be formed in separate components which are subsequently assembled. The connection between connector 910 and arms 912, 914 forms two living hinges 916, 918. The living hinges 916, 918 allow lateral engagement surfaces 906, 908 to flex away from each other. Arms 912, 914 are provided with registration grooves 930, 932 to align the guide, with the guide tool 950.

Arms 912, 914 comprise lateral engagement surfaces 906, 908 distal of connector 910 to engage the spinous process while centering guide bore 902 on the apex of the spinous process. Lateral engagement surfaces 906, 908 are provided with gripping, elements 924, 925, 926, 927 to better grip the spinous process. In this embodiment, gripping elements 924, 925, 926, 927 comprise spikes formed on lateral engagement surfaces 906, 908. Arms 912, 914 are shaped so as to conform to the lateral surfaces of the spinous process. Arms 912, 914 or a portion thereof may be formed from a flexible and/or compressible material to better conform to the lateral surfaces of the spinous process. As shown in FIG. 9A arms 912, 914 are tapered and radiussed for ease of insertion over a spinous process 252. In the unflexed configuration, arms 912, 914 are further apart than the width of the apex of a spinous process and the sides of a spinous process as shown in FIG. 9A.

Referring again to FIG. 9A, guide tool 950 is formed from a relatively inflexible material such as surgical stainless steel or titanium. The guide tool 950 has a guide tool bore 952 in connector 960. Guide tool 950 comprises two arms 962, 964 which comprise engagement surfaces 956, 958 distal of connector 960 to engage the exterior of guide 900 while centering guide tool bore 952 on the apex of the spinous process. Arms 962, 964 are sized such they slide over connector 910 of guide 900. In this embodiment, arms 962, 964 may be formed in one piece with connector 952 disposed between them or the arms and connector may be formed in separate components which are subsequently assembled. The connection between connector 960 and arms 962, 964 is inflexible such that the arms 916, 918 are in a fixed parallel relationship. Arms 962, 964 are provided with registration guides 980, 982 which are designed to ride in registration grooves 930, 932 of guide 900 as guide tool 950 slides over guide 900.

Referring in to FIG. 9B, guide tool arms 960, 962 are made from a relatively inflexible material such that they maintain their fixed parallel relationship to one another as they slide over arms 912, 914 of guide 900. Thus, when guide tool 950 slides over guide 900 in the direction of arrow 920, arms 960, 962 of guide tool 950 engage arms 912, 914 of guide 900 forcing lateral engagement surfaces 906, 908 towards each other in the direction of arrows 921, 922. With guide 900 in position with apex engagement surface 904 in contact with apex 254 or spinous process 252, guide tool 950 forces lateral engagement surfaces 906, 908, and gripping elements 924, 925, 926, 927 of arms 912, 914 of guide 900 into contact with the lateral surfaces of spinous process 252. This secures guide 900 to spinous process 252 and centers guide bore 902 and guide tool bore 952 on the apex of spinous process 252. Note that the guide tool bore 952 is in registration with the guide bore 902 of guide 900.

Figure 10A:
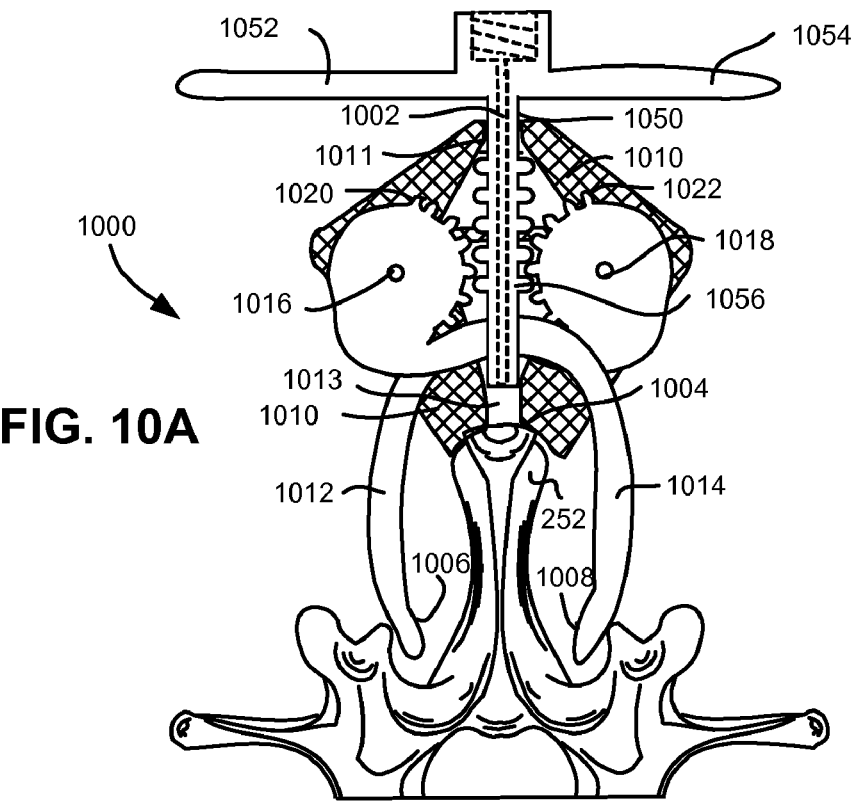
FIG. 10A shows a plan view of an guide in accordance with one embodiment of the present invention.
Figure 10B:
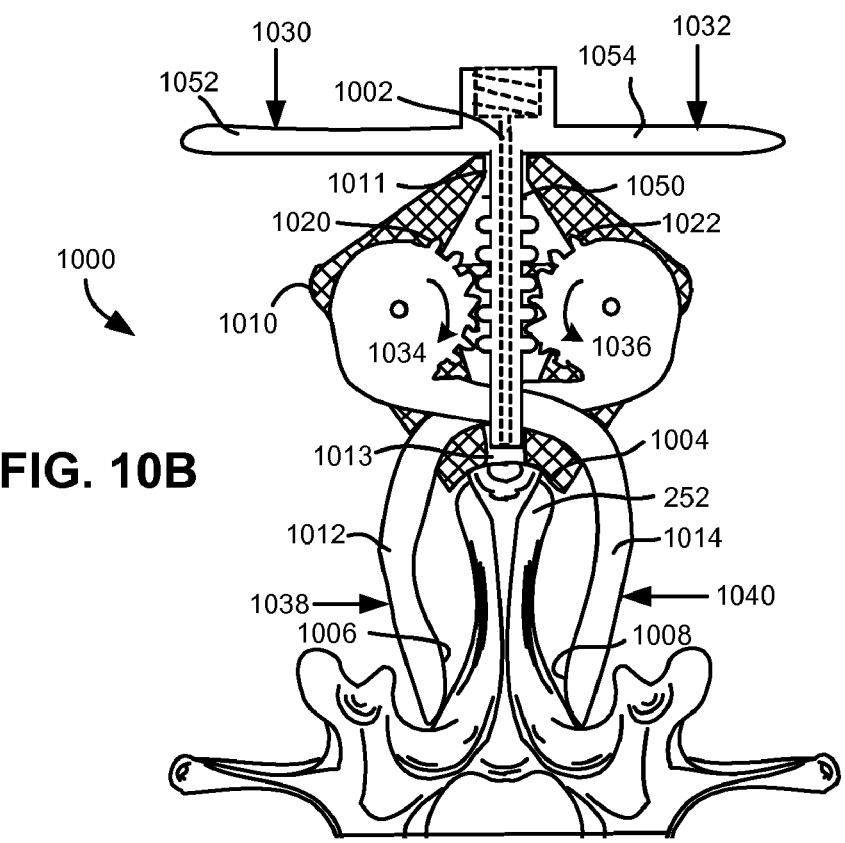
FIG. 10B shows a plan view of the guide of FIG. 10A in the deployed configuration.

FIGS. 10A-B illustrate two views of another embodiment of a guide in accordance the present invention. FIG. 10A shows a side view of a multi-component guide 1000 which has a guide bore 1002 in central tube 1050. Central tube 1050 is also connected to handles 1052, 1054. Central tube 1050 is slidingly retained in bores 1011, 1013 of connector 1010. Between bores 1011, 1013 central tube 1050 comprise a toothed section 1056. Connector 1010 comprises a curved apex engagement surface 1004 for engaging the apex of a spinous process 252. Guide bore 1002 acts as a position and direction guide for introduction of a needle or other surgical instrument. Guide 1000 may also serve as a depth guide to limit the depth of insertion of a needle or surgical instrument into a spinous process.

Guide 1000 also comprises two arms 1012, 1014 to engage the spinous process while centering guide bore 1002 on the apex of the spinous process 252. Arms 1012, 1014 are connected by pivots 1016, 1018 to connector 1010. Each of arms 1012, 1014 has a toothed perimeter 1020, 1022 which engages toothed section 1056 of central tube 1050. Arms 1012, 1014 comprise lateral engagement surfaces 1006, 1008 to engage the spinous process while centering guide bore 1002 on the apex of the spinous process 252.

As shown in FIG. 10A, apex engagement surface 1004 may be placed in contact with the apex of a spinous process 252 with arms 1012, 10014 spaced away from spinous process 252. As shown in FIG. 10B, when a force is applied to handles 1052, 1054 in the direction shown by arrows 1030, 1032 central tube 1050 slides towards spinous process 252 through bores 1011, 1013 in connector 1010. Toothed perimeters 1020, 1022 of arms 1006, 1008 are engaged by toothed section 1056 of central tube 1050 causing the arms to pivot in the directions shown by arrows 1034, 1036. Lateral engagement surfaces 1006, 1008 are thereby urged in the direction of arrows 1038, 1040, into contact with spinous process 252. Thus, pushing down on handles 1052, 1054 pushes apex engagement surface 1004 and lateral engagement surfaces 1006, 1008 into contact with spinous process 922 centering bore 1002 with the axis of spinous process 252.

Figure 11A:
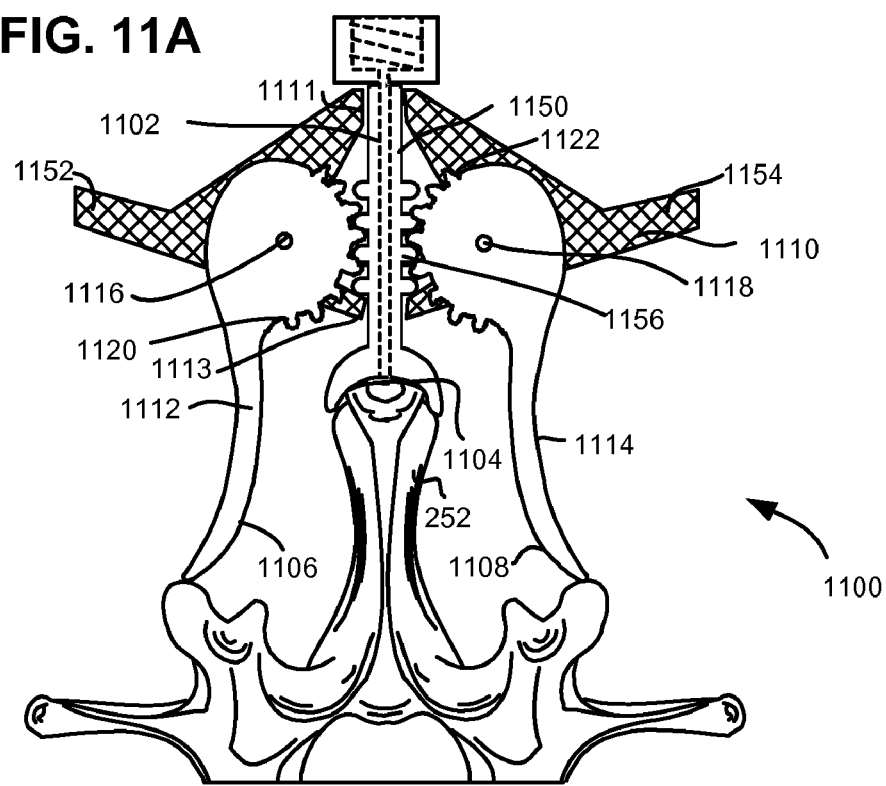
FIG. 11A shows a plan view of an guide in accordance with one embodiment of the present invention.
Figure 11B:
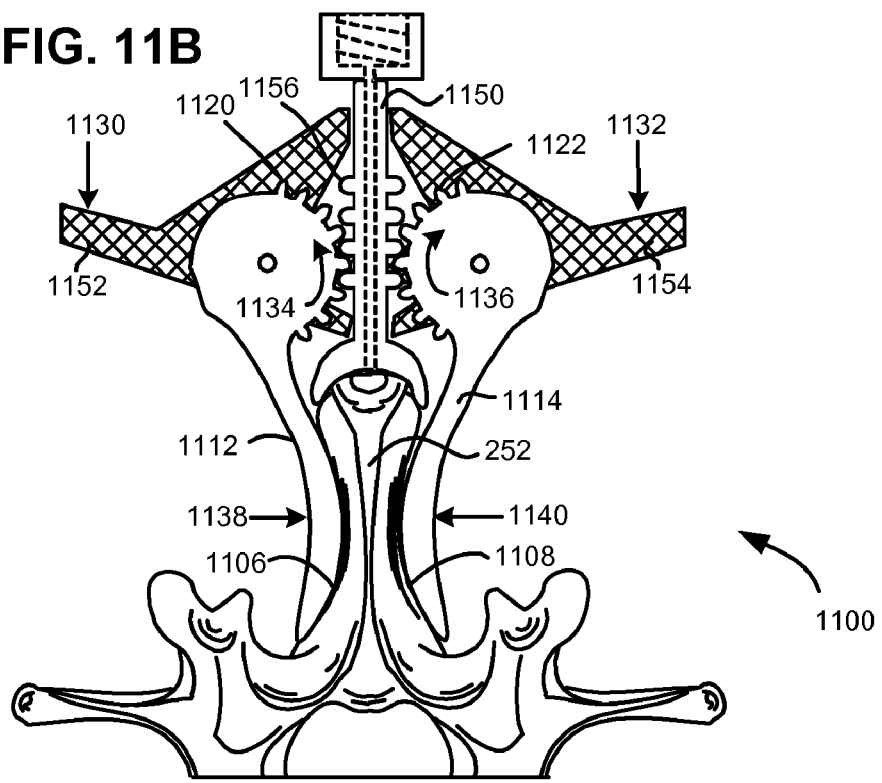
FIG. 11B shows a plan view of the guide of FIG. 11A in the deployed configuration.

FIGS. 11A-B illustrate another embodiment of a guide in accordance with the present invention. FIG. 11A shows a side view of a multi-component guide 100 which has a guide bore 1102 in central tube 1150. Central tube 1150 comprises a curved apex engagement surface 1104 for engaging the apex of a spinous process. Central tube 1150 is slidingly retained in bores 1111, 1113 of connector 1110. Between bores 1111, 1113 central tube 1150 comprise a toothed sectional 1156. Connector 1110 is also connected to handles 1152, 1154. Guide bore 1102 acts as a position and direction guide for introduction of a needle or other surgical instrument. Guide 1100 may also serve as a depth guide to limit the depth of insertion of a needle to surgical instrument into a spinous process.

Guide 1100 also comprises two arms 1112, 1114. The arms 1112, 1114 comprise lateral engagement surfaces 1106, 1108 to engage the spinous process while centering guide bore 1102 on the apex of the spinous process. Arms 1112, 1114 are connected by pivots 1116, 1118 to connector 1110. Each of arms 1112, 1114 has a toothed perimeter 1120, 1122 which engages toothed section 1156 of central tube 1150.

As shown in FIG. 11A, apex engagement surface 1104 may be placed in contact with the apex of spinous process 252 with lateral engagement surfaces 1106, 1108 spaced away from spinous process 252. As shown in FIG. 11B, when a force is applied to handles 1152, 1154 in the direction of arrows 1130, 1132 connector 1110 slides towards spinous process 252 as central tube 1150 slides through bores 1111, 1113 in connector 1110. Toothed perimeters 1120, 1122 of arms 1106, 1108 are engaged by central tube 1150 causing the arms to pivot in the directions shown by arrows 1134, 1136. Thus, lateral engagement surfaces 1106, 1108 are urged in the direction of arrows 1138, 1140, into contact with spinous process 252. Thus, pushing down on handles 1152, 1154 pushes apex engagement surface 1104 and lateral engagement surfaces 1106, 1108 into contact with spinous process 252 centering bore 1102 with the axis of spinous process 252.

Figure 12A:
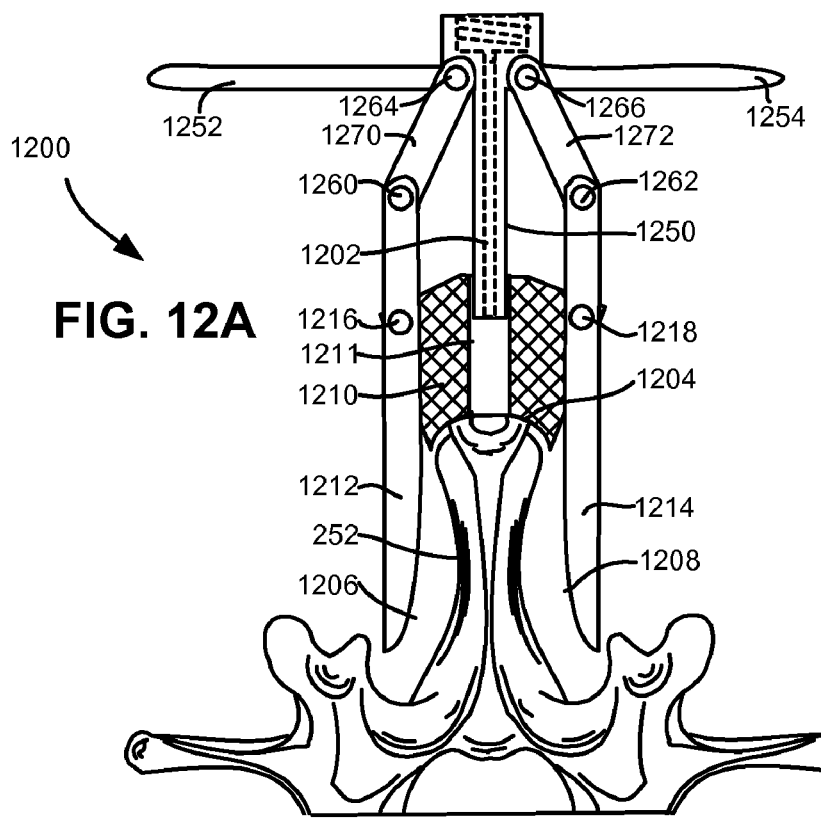
FIG. 12A shows a plan view of an guide in accordance with one embodiment of the present invention.
Figure 12B:
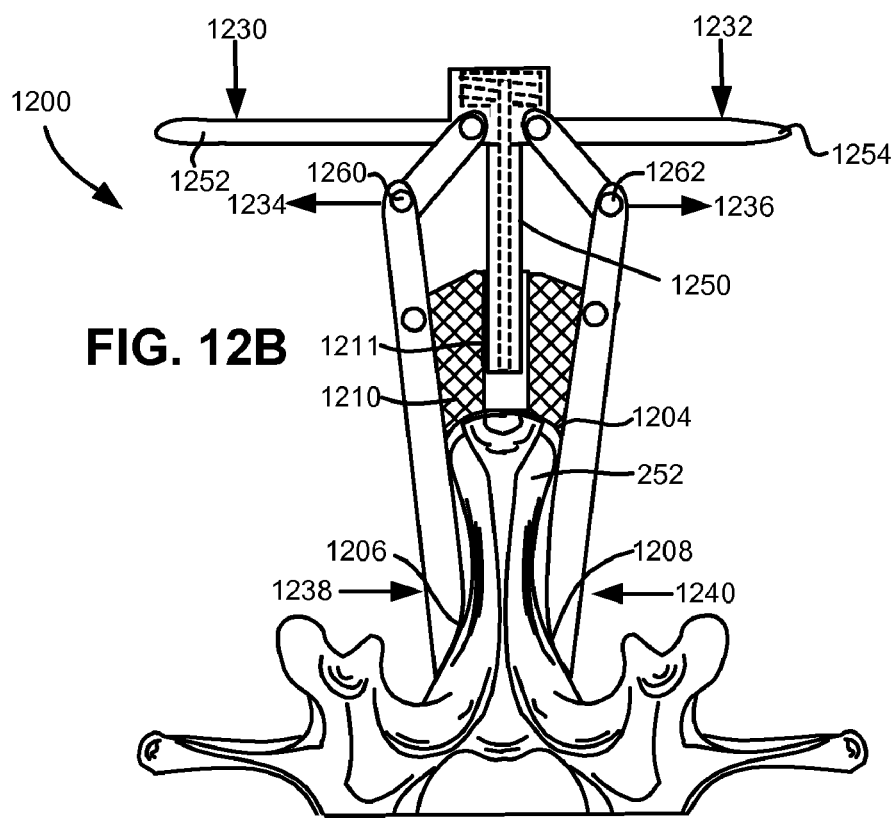
FIG. 12B shows a plan view of the guide of FIG. 12A in the deployed configuration.

FIGS. 12A-B illustrate two views of another embodiment of a guide in accordance with the present invention. FIG. 12A shows a side view of a multi-component guide 1200 which has a guide bore 1202 in central tube 1250. Central tube 1250 is also connected to handles 1252, 1254. Central tube 1250 is slidingly retained in bore 1211 of connector 1210. Connector 1210 comprises a curved apex engagement surface 1204 for engaging the apex of a spinous process. Guide bore 1202 acts as a position and direction guide for introduction of a needle or other surgical instrument. Guide 1200 may also serve as a depth guide to limit the depth of insertion of a needle or surgical instrument into a spinous process.

Guide 1200 also comprises two arms 1212, 1214. The arms 1212, 1214 comprise lateral engagement surfaces 1206, 1208 to engage the spinous process while centering guide bore 1202 on the apex of the spinous process 252. Arms 1212, 1214 are connected by pivots 1216, 1218 to connector 1210. Arm 1212 is connected by pivot 1260 to arm 1270 which is connected by pivot 1264 to central tube 1250. Arm 1214 is connected by pivot 1262 to arm 1272 which is connected by pivot 1266 to central tube 1250.

As shown in FIG. 12A, apex engagement surface 1204 may be placed in contact with the apex of spinous process 252 with lateral engagement surfaces 1206, 1208 spaced away from spinous process 252. As shown in FIG. 12B, when a force is applied to handles 1252, 1254 in the direction shown by arrows 1230, 1232 central tube 1250 slides towards spinous process 252 through bore 1211 in connector 1210. As central tube 1250 slides towards spinous process 252, pivots 1260, 1262 are pushed outwards in the direction of arrows 1234, 1236 and lateral engagement surfaces 1206, 1208 are pushed in the direction of arrows 1238, 1240. Thus, lateral engagement surfaces 1206, 1208 are urged in the direction of arrows 1238, 1240, into contact with spin oils process 252. Thus, pushing down on handles 1252, 1254 pushes apex engagement surface 1204 and lateral engagement surfaces 1206, 1208 into contact with spinous process 252 centering bore 1202 with the axis of spinous process 252.

Figure 13A:
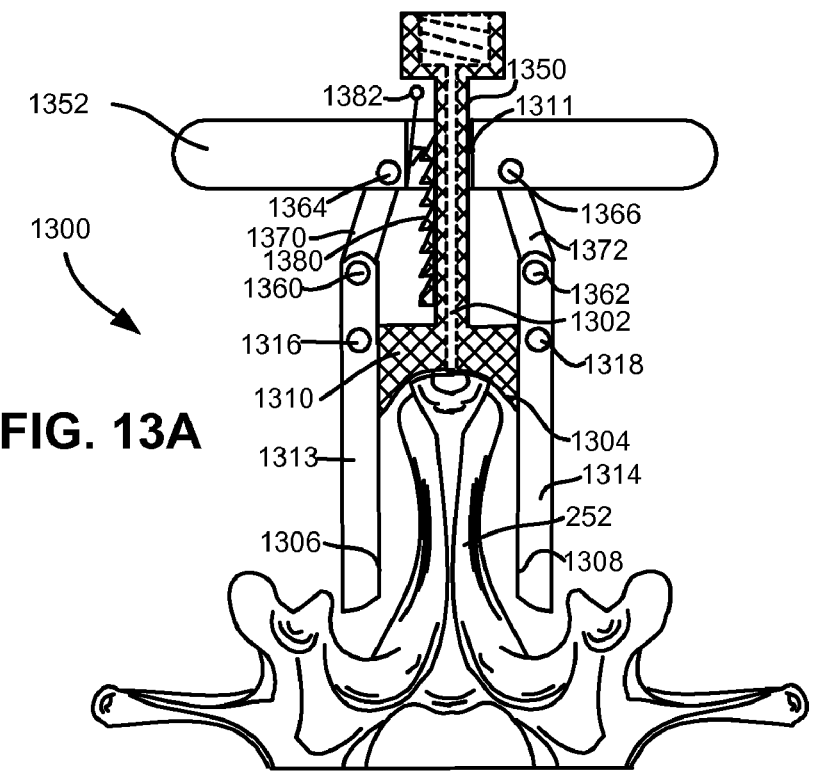
FIG. 13A shows plan view of an guide in accordance with one embodiment of the present invention.
Figure 13B:
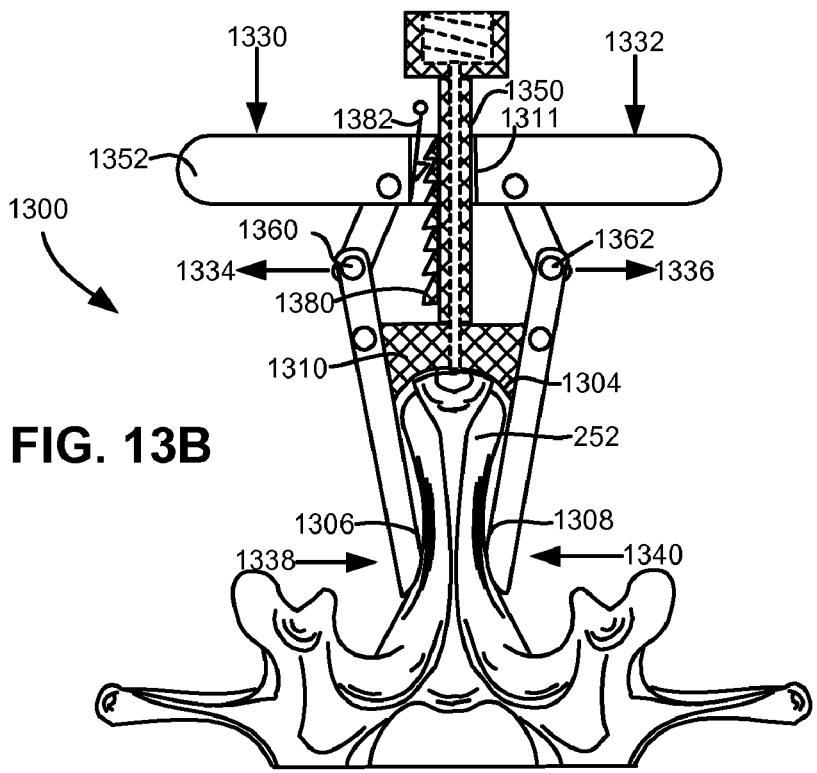
FIG. 13B shows a plan view of the guide of FIG. 13A in the deployed configuration.

FIGS. 13A-B illustrate two views of another embodiment of a guide in accordance with the present invention. FIG. 13A shows a side view of a multi-component guide 1300 which has a guide bore 1302 in central tube 1350. Central tube 1350 sides within bore 1311 of handle 1352. Central tube 1350 is connected to connector 1310. Connector 1310 comprises a curved apex engagement surface 1304 for engaging the apex of a spinous process 252. Guide bore 1302 acts as a position and direction guide for introduction of a needle or other surgical instrument. Guide 1300 may also serve as a depth guide to limit the depth of insertion of a needle or surgical instrument into a spinous process.

Guide 1300 also comprises two arms 1312, 1314. The arms 1312, 1314 comprise lateral engagement surfaces 1306, 1308 to engage the spinous process while centering guide bore 1302 on the apex of the spinous process. Arms 1312, 1314 are connected by pivots 1316, 1318 to connector 1310. Arm 1312 is connected by pivot 1360 to arm 1370 which is connected by pivot 1364 to handle 1352. Arm 1314 is connected by pivot 1362 to arm 1372 which is connected by pivot 1366 to handle 1352.

As shown in FIG. 13A, apex engagement surface 1304 may be placed in contact with the apex of spinous process 252 with lateral engagement surfaces 1306, 1308 spaced away from spinous process 252. As shown in FIG. 13B, when a force is applied to handle 1352 in the direction shown by arrows 1330, 1332 handle 1352 slides towards spinous process 252 as central tube 1350 slides through bore 1311 in handle 1352. As handle 1352 slides towards spinous process 252, pivots 1360, 1362 are pushed outwards in the direction of arrows 1334, 1336 and lateral engagement surfaces 1306, 1308 are pushed in the direction of arrows 1338, 1340. Thus, lateral engagement surfaces 1306, 1308 are urged in the direction of arrows 1338, 1340, into contact with spinous process 252. Thus, pushing down on handle 1352 pushes apex engagement surface 1304 and lateral engagement surfaces 1306, 1308 into contact with spinous process 252 centering bore 1302 with the axis of spinous process 252.

Also shown in FIG. 13B is ratchet 1380 and ratchet release 1382. The ratchet locks the handle 1352 in position, thereby locking engagement surfaces 1306, 1308 against spinous process 252 during needle insertion. When the guide 1300 is to be removed, ratchet release 1382 can disengage ratchet 1380 allowing the engagement surfaces 1306, 1308 to be drawn back from spinous process 252. A similar ratchet or other surgical instrument locking mechanism may be adapted for us in each of the guides of FIGS. 10A-B, 11A-B, and 12A-B.

Procedures Utilizing Spinous Process Reinforcement

The methods described above may be used to strengthen the spinous process to guard against damage to the spinous process or repair trauma to the spinous process. However, as previously stated, the method of the present invention is particularly advantageous when utilized in combination with other interventions that interact with the spinous process. An example of such a procedure is the X-STOP™ procedure in which a spinous process distractor is inserted between the spinous processes of adjacent vertebrae as shown in FIG. 1. Distraction of the spinous processes serves to relieve problems caused by spinal stenosis. This procedure and implant is described in detail in U.S. Pat. No. 7,779,842 to Zucherman et al. titled, "Spine Distraction Implants" which is incorporated herein by reference. The method of the present invention may be used in combination with such a procedure to reinforce one or more spinous processes. This method will thus make interventions such as the X-STOP™ procedure available to a wider range of patients and enhance the outcome of such procedures.

In practice, the method of the present invention may be used to reinforce each spinous process that will be adjacent to the distractor. Thus, as shown in FIG. 1, bone cement may be injected into both spinous processes 102 and 103. To minimize the number of procedures and discomfort to the patient, the reinforcing procedure and distractor implant procedure may be performed in a single procedure. First, each spinous process is located and bone cement is injected as previously described. Next, the bone cement is allowed to harden. Next the distractor is implanted between the reinforced spinous processes as described in U.S. Pat. No. 7,779,842.

Although, the use of the invention has been described with respect to the X-STOP™ it will be apparent that the reinforcement of the spinous process would likewise be a useful part of any spinal intervention which interacts with the spinous process. Such procedures include for example procedures where implants are bolted to the spinous process, or where screws are inserted into the spinous process, or where distraction or fixation of spinous processes is performed.

Materials for Guides and Reinforcing Elements

In some embodiments, the reinforcing elements and guide or portions thereof can be fabricated from medical grade metals such as titanium stainless steel, cobalt chrome, and alloys thereof, or other suitable guide material having similar high strength and biocompatible properties. Additionally, the guide can be at least partially fabricated from a shape memory metal, for example Nitinol, which is a combination of titanium and nickel. Such materials are typically radiopaque, and appear during x-ray imaging, and other types of imaging.

In some embodiments the reinforcing elements and guide or portions thereof can be fabricated from somewhat flexible and/or deflectable material. In these embodiments, the guide and/or portions thereof can be fabricated in whole or in part from medical grade biocompatible polymers, copolymers, blends, and composites of polymers. A copolymer is a polymer derived from more than one species of monomer. A polymer composite is a heterogeneous combination of two or more materials, wherein the constituents are not miscible, and therefore exhibit an interface between one another. A polymer blend is a macroscopically homogeneous mixture of two or more different species of polymer. The reinforcing elements and guide and/or portions thereof can be formed by extrusion, injection, compression molding and/or machining techniques.

Many polymers, copolymers, blends, and composites of polymers are radiolucent and do not appear during x-ray or other types of imaging. Guides comprising such materials can provide a physician with a less obstructed view of the spine under imaging, than with a guide comprising radiopaque materials entirely. For example, if the guide is radiolucent, the surgeon will be better able to visualize the needle for injecting bone cement. The surgeon will also be better able to visualize the bone cement during injection. To allow visualization, it is preferable that at least a portion of the guide surrounding the spinous process be radiolucent. However, the guide may be formed in part or whole from radio-opaque materials such as the metals identified above.

One group of biocompatible polymers is the polyaryl ester ketones which has several members including polyetheretherketone (PEEK), and polyetherketoneketone (PEKK). PEEK is proven as a durable material for guides, and meets the criterion of biocompatibility. Medical grade PEEK is available from Victrex Corporation of Lancashire, Great Britain under the product name PEEK-OPTIMA. Medical grade PEKK is available from Oxford Performance Materials under the name OXPEKK, and also from CoorsTek under the name BioPEKK. These medical grade materials are also available as reinforced polymer resins, such reinforced resins displaying even greater material strength. In some embodiments, the guides and/or reinforcing elements can be fabricated from PEEK 450G, which is an unfilled PEEK approved for medical implantation available from Victrex. Other sources of this material include Gharda located in Panoli, India. PEEK 450G has the following approximate properties:

| Property | Value |
| --- | --- |
| Density | 1.3 g/cc |
| Rockwell M | 99 |
| Rockwell R | 126 |
| Tensile Strength | 97 MPa |
| Modulus of Elasticity | 3.5 GPa |
| Flexural Modulus | 4.1 GPa |

It should be noted that the material selected can also be filled. Fillers can be added to a polymer, copolymer, polymer blend, or polymer composite to reinforce a polymeric material. Fillers are added to modify properties such as mechanical, optical, and thermal properties. For example, carbon fibers can be added to reinforce polymers mechanically to enhance strength for certain uses, such as for load bearing devices. In some embodiments, other grades of PEEK are available and contemplated for use in guides in accordance with the present invention, such as 30% glass-filled or 30% carbon-filled grades, provided such materials are cleared for use in implantable devices by the FDA, or other regulatory body. Glass-filled PEEK reduces the expansion rate and increases the flexural modulus of PEEK relative to unfilled PEEK. The resulting product is known to be ideal for improved strength, stiffness, or stability. Carbon-filled PEEK is known to have enhanced compressive strength and stiffness, and a lower expansion rate relative to unfilled PEEK. Carbon-filled PEEK also offers wear resistance and load carrying capability.

As will be appreciated, other suitable similarly biocompatible thermoplastic or thermoplastic polycondensate materials that resist fatigue, have good memory, are flexible, and/or deflectable, have very low moisture absorption, and good wear and/or abrasion resistance, can be used without departing from the scope of the invention. As mentioned, the guide can be comprised of polyetherketoneketone (PEKK). Other materials that can be used include polyetherketone (PEK), polyetherketone-etherketoneketone (PEKEKK), polyetheretherketoneketone (PEEKK), and generally a polyaryletheretherketone. Further, other polyketones can be used as well as other thermoplastics. Reference to appropriate polymers that can be used in the guide and/or reinforcing elements can be made to the following documents, all of which are incorporated herein by reference. These documents include: PCT Publication WO 02/02158 A1, dated Jan. 10, 2002, entitled "Bio-Compatible Polymeric Materials;" PCT Publication WO 02/00275 A1, dated Jan. 3, 2002, entitled "Bio-Compatible Polymeric Materials;" and, PCT Publication WO 02/00270 A1, dated Jan. 3, 2002, entitled "Bio-Compatible Polymeric Materials." Other materials such as Bionate®, polycarbonate urethane, available from the Polymer Technology Group, Berkeley, Calif., may also be appropriate because of the good oxidative stability, bicompatibility, mechanical strength and abrasion resistance. Other thermoplastic materials and other high molecular weight polymers suitable for surgical instruments can also be used for the guide.

Bone Cement Compositions and Bone Cement Tools

As described above, objects of the present invention are accomplished by injecting a flowable reinforcing, bone filler material, such as bone cement, into a fractured, weak, or diseased spinous process and lamina. Bone cement materials typically include a solid finely-divided powder or granular polymer component and a liquid reactive or polymerizable monomer component which is also a solvent or swelling agent for the polymer component. The polymer and monomer components can be based on the acrylic, e.g., (meth)acrylate system, however, other polymeric systems can also be used. The polymer component of the composition can be any methyl(meth)acrylate polymer. The reactive monomer component is preferably methyl acrylate or methyl methacrylate. These bone cement materials are mixed together with a polymerization catalyst and a polymerization accelerator immediately prior to use to form a viscous fluid which may be injected into a spinous process. The bone cement hardens in-situ via an exothermic reaction within a few minutes depending upon the particular composition used.

Alternative bone cement compositions include injectable calcium phosphate systems. Typical calcium phosphate bone cement comprises a dry powder of a mixture of acidic and basic calcium phosphate particles and a liquid containing phosphate solution. Additional components are generally required to make the cement flowable and injectable. One such cement is disclosed in Komath et al., "Development Of A Fully Injectable Calcium Phosphate Cement For Orthopedic And Dental Applications," Bull. Mater. Sci., Vol. 26. No. 4, June 2003, pp. 415-422 which is incorporated herein by reference.

Bone cement may be further modified by the addition of crystalline and/or fibrous materials to the bone cement to reinforce the bone cement. Possible bone-cement-strengthening materials for modifying the bone cement include metal fibers (such as titanium fibers and steel fibers) and non-metallic fibers (such as carbon fibers and polymer fibers). The crystalline and/or fibrous materials should be biocompatible and small enough that they do impair the flowability or injectability of the bone cement. A number of bone-cement-strengthening materials are disclosed in U.S. patent application Ser. No. 10/936,188 entitled, "Bone Cement Compositions Having Fiber-Reinforcement And/Or Increased Flowability" by Armitage et al., which is incorporated herein by reference.

A radio-opaque material, such as barium sulfate, is usually added to bone cement in order to allow x-ray visualization during injection. In spinous process reinforcement only a small amount of bone cement is injected, typically from 1-5 cc per spinous process, more particularly from 1 to 3 cc. A much later amount is usually injected in other orthopedic applications which typically require from 40 to 100 cc. The smaller volume of bone cement injected into a spinous process is harder to visualize. Therefore, it may be necessary to use a bone cement mixture with higher levels of radio-opaque materials as compared to standard orthopedic bone cement mixtures. A number of the commercially-available bone cements listed below have increased radio-opacity and are specially-designed to facilitate visualization in low volume applications.

Commercially-available bone cement materials suitable for use in accordance with various embodiments of the present invention include, but are not limited to: AVA-TEX® Bone Cement from Cardinal Health Inc. of Dublin Ohio; CEMEX™ Bone Cement from. Exactech Inc. of Gainesville Fla.; CEMFIX™ and GENTAFIX™ Bone Cement from Mathys AG of Bettlach Switzerland; CONCERT® Bone Cement from Advanced Biomaterial Systems of Chatham, N.J.; CORIPLAST™ Bone Cement from Corin Group, PLC of Gloustershire, Unite Kingdom; CORTOSS® Bone Cement from Orthovita, Inc. of Malvern, Pa.; DEPUY™ Bone Cement from DePuy Orthopaedics of Warsaw, Ind.; KyphX® HV-R™ (High-Viscosity Radiopaque) Bone Cement from Kyphon, Inc. of Sunnyvale, Calif.; ORTHOSET® Radiopaque Bone Cement from Wright Medical Technology, Inc. of Arlington Tenn.; PALACOS® Bone Cement from Biomet Orthopedics, Inc. of Warsaw, Ind.; PARALLAX® Bone Cement from Arthrocare Spine, Inc. of Sunnyvale, Calif.; SOMATEX® Medical Technologies GmbH of Teltow, Germany; SPINEPLEX™ and SIMPLEX™ Bone Cement from Stryker Corporation of Kalamazoo, Mich.; VERSABOND™ Bone Cement from Smith & Nephew, Inc.—Orthopaedics of Memphis Tenn.; and Zimmer® Osteobond™ Bone Cement from Zimmer, Inc. of Warsaw, Ind.

Most vendors of bone cement also sell devices for mixing and injecting bone cement. Commercially-available injectors and mixers for use in accordance with various embodiments of the present invention include, but are not limited to: the AVA-TEX™ Bone Cement Delivery System from Cardinal Health, Inc. of Dublin Ohio; the BOCEMIX Bone Cement Mixer from BIDOIA SAS of Padova, Italy; the PLEXIS® Bone Void Filling System from Advanced Biomaterial Systems of Chatham, N.J.: HIVAC™ and MINIMIX Bone Cement Mixing Systems from Summit Medical Ltd. Of Gloustershire, United Kingdom; the KYPHON® Mixer from Kyphon, Inc. of Sunnyvale, Calif.; the OsteoJect™ Bone Cement Delivery System from Integra Life Sciences, Inc. of Plainsboro, N.J.; the SOMIX® bone cement mixer from SOMATEX® Medical Technologies GmbH of Teltow, Germany and the SPLINEPLEX™ Percutaneous Cement Delivey System and Advanced Cement Mixing (ACM) System from Stryker Corporation of Kalamazoo, Mich.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

We claim:

1. A guide for use in a procedure to introduce a surgical instrument having an insertion axis and a distal tip along a desired axis of a spinous process of a vertebra wherein the guide comprises:
    a first arm comprising a first guide surface adapted to engage the spinous process;
    a second arm comprising a second guide surface adapted to engage the spinous process;
    an apex engagement surface adapted to engage an apex of the spinous process;
    a handle operatively coupled to the first arm and the second arm;
    a guide bore adapted to allow passage of the surgical instrument; and
    wherein the handle is operative to change a distance between the first guide surface and the second guide surface and the guide bore is adapted to control the insertion axis of the instrument such that engagement of the spinous process by the apex engagement surface, the first guide surface and the second guide surface aligns the insertion axis of the instrument with the desired axis of the spinous process.

2. The guide of claim 1, wherein:
    the handle comprises a first handle element connected to the first arm and a second handle element connected to the second arm;
    and wherein the first arm is pivotally connected to the second arm such that the distance between the first guide surface and the second guide surface is increased when the distance between the first handle element and the second handle element is decreased.

3. The guide of claim 1, further comprising:
    a spring element which biases the first side surface towards the second guide surface;

and wherein the handle is operative to increase the distance between the first guide surface and the second guide surface against the biasing of the spring element.

4. The guide of claim 1, wherein:
the handle is movably connected to the arms such that the distance between the first guide surface and the second guide surface is decreased when the handle is pushed towards the first arm and second arm.

5. The guide of claim 1, further comprising:
a lock element which maintains the distance between the first guide surface and the second guide surface.

6. The guide of claim 5, wherein the lock element includes a plurality of detent positions to selectively maintain the distance between the first guide surface and the second guide surface.

7. The guide of claim 5, further comprising:
a release element which may be operated to release the lock element such that the distance between the first guide surface and the second guide surface is no longer maintained.

8. The guide of claim 1, further comprising a connector wherein at least one of the first and second arms is flexibly joined to the connector and wherein the handle is operatively connected to the fists arm and second arm such that in a first configuration the first surface and second surface are spaced sufficiently far apart to allow the guide to be positioned over the apex of a spinous process and in a second configuration, the first surface and second surface are spaced sufficiently close together to be biased against the sides of the spinous process.

9. The guide of claim 1, wherein the guide is releasably connected to an implantable spinous process reinforcing element.

10. The guide of claim 1, wherein the guide comprises a releasable implantable mesh reinforcing element.

11. A kit for use in a procedure to reinforce a spinous process, the kit comprising:
a guide;
a reinforcing element; and
a surgical instrument;
wherein the surgical instrument has an insertion axis, a distal tip and a bore through which a flowable reinforcing material may be injected into the spinous process;
wherein the guide has a guide bore adapted to allow insertion, passage, and removal of the surgical instrument along the insertion axis; and
wherein the guide comprises a first guide surface and a second guide surface adapted to engage the spinous process and align the guide bore with the spinous process.

12. The kit of claim 11, wherein:
the reinforcing element is releasably connected to the guide such that the reinforcing element is positioned with respect to the spinous process when the first guide surface and the second guide surface engage the spinous process.

13. The kit of claim 11, wherein:
the reinforcing element is adapted to be inserted into the spinous process through the guide bore.

14. The kit of claim 11, wherein:
the reinforcing element is adapted to be placed around the spinous process.

15. The kit of claim 11, wherein:
the reinforcing element comprises one of a titanium clip; a titanium tube, a titanium rod and a titanium screw.

16. The kit of claim 11 wherein:
the guide and the surgical instrument are sized so as to prevent insertion of the surgical instrument surgical through the guide into a spinal canal of the patient.

17. The kit of claim 11, wherein the guide comprises:
a handle comprising a first handle element connected to the first surface and a second handle element connected to the second surface such that the handle may be operated to cause the first surface and the second surface to be biased against the sides of the spinous process.

18. The kit of claim 11, wherein the guide comprises:
a spring element which biases the first side surface towards the second guide surface;
and wherein the handle is operative to increase the distance between the first guide surface and the second guide surface against the biasing of the spring element.

19. The kit of claim 11, wherein the guide comprises:
a handle is movably connected to the arms such that the distance between the first guide surface and the second guide surface is decreased when the handle is pushed towards the first arm and second arm.

20. The kit of claim 11, wherein the guide comprises:
a lock element which maintains the distance between the first guide surface and the second guide surface.

21. A method for strengthening a spinous process of a vertebra having a lamina wherein the method comprises:
(a) inserting a guide over the spinous process;
(b) operating the guide to grasp the spinous process;
(c) inserting a surgical instrument having a bore through the guide into the spinous process; and
(d) forcing a flowable reinforcing material through the tubular bore such that it flows into the spinous process.

22. The method of claim 21, wherein the guide comprises a first guide surface and a second guide surface and wherein:
step (a) includes positioning the first guide surface and the second guide surface adjacent first and second sides of a spinous process;
step (b) includes operating the guide such that the first guide surface and the second guide surface grasp the first and second sides of the spinous process.

23. The method of claim 21, wherein the guide further comprises a handle, a first guide surface and a second guide surface and wherein:
step (a) includes positioning the first guide surface and the second guide surface adjacent first and second sides of a spinous process;
step (b) includes operating the handle of the guide such that the first guide surface and the second guide surface grasp the first and second sides of the spinous process.

24. The method of claim 21, wherein the guide comprises a guide bore and wherein:
step (c) comprises inserting the surgical instrument through the guide bore.

25. The method of claim 21, wherein the guide comprises a first guide bore and a second guide bore and step (c) comprises inserting the surgical instrument through the first guide bore and wherein the method further comprises:
(d) removing the surgical instrument from the first guide bore;
(e) inserting the surgical instrument through the second guide bore; and
(f) forcing a flowable reinforcing material through the tubular bore such that it flows into the spinous process.

26. The method of claim 21, further comprising:
(e) inserting an implantable reinforcing element into the spinous process.

27. The method of claim 21, further comprising:
(e) placing, an implantable reinforcing element around the spinous process.

28. The method of claim 21, further comprising:
(e) placing an implantable reinforcing element in contact with the spinous process;
(f) removing the guide, while the reinforcing element is retained in contact with the spinous process.

29. The method of claim 21, further comprising:
(e) operating the guide to release the spinous process.

30. The method of claim 28, wherein the guide further comprises a handle, a first guide surface and a second guide surface and wherein:
   step (a) includes positioning the first guide surface and the second guide surface adjacent first and second sides of a spinous process;
   step (b) includes operating the handle such that the first guide surface and the second guide surface grasp the first and second sides of the spinous process; and
   step (c) includes operating the handle such that the first guide surface and the second guide surface release the first and second sides of the spinous process.

31. The method of claim 28, wherein the guide further comprises a handle, a lock, a first guide surface and a second guide surface and wherein:
   step (a) includes positioning the first guide surface and the second guide surface adjacent first and second sides of a spinous process;
   step (b) includes operating the handle such that the first guide surface and the second guide surface grasp the first and second sides of the spinous process; and
   step (e) includes releasing the lock such that the first guide surface and the second guide surface release the first and second sides of the spinous process.

* * * * *